(12) United States Patent
Dunayevskiy et al.

(10) Patent No.: US 6,299,747 B1
(45) Date of Patent: Oct. 9, 2001

(54) CAPILLARY ELECTROPHORETIC METHODS TO DETECT NEW BIOLOGICALLY ACTIVE COMPOUNDS IN COMPLEX BIOLOGICAL MATERIAL

(75) Inventors: Yuriy M. Dunayevskiy, Natick; James L. Waters, Framingham; Dallas E. Hughes, Westboro, all of MA (US)

(73) Assignee: Cetek Corporation, Marlborough, MA (US)

( * ) Notice: Subject to any disclaimer, the term of this patent is extended or adjusted under 35 U.S.C. 154(b) by 0 days.

(21) Appl. No.: 09/162,586

(22) Filed: Sep. 29, 1998

Related U.S. Application Data

(60) Provisional application No. 60/069,943, filed on Dec. 17, 1997.

(51) Int. Cl.$^7$ .................. G01N 27/26; G01N 27/447; G01N 33/537; G01N 33/541; G01N 33/561

(52) U.S. Cl. .................. 204/451; 204/451; 204/600; 436/516; 436/538; 436/540

(58) Field of Search .................. 204/601, 602, 204/603, 604, 605, 451, 452, 453, 455, 606, 607, 608, 610, 612, 615, 616, 617, 618, 621; 436/516, 536, 538, 540

(56) References Cited

U.S. PATENT DOCUMENTS

| | | | |
|---|---|---|---|
| 5,228,960 | 7/1993 | Liu et al. | 204/451 |
| 5,234,586 | 8/1993 | Afeyan et al. | 210/198.2 |
| 5,431,793 | 7/1995 | Wang et al. | 204/452 |
| 5,536,382 | 7/1996 | Sunzeri | 204/451 |
| 5,567,282 | 10/1996 | Wang et al. | 204/450 |
| 5,783,397 | * 7/1998 | Hughes et al. | 435/7.1 |

FOREIGN PATENT DOCUMENTS

| | | |
|---|---|---|
| 0 572 023 A2 | 5/1993 | (EP) . |
| 9106850 | 5/1991 | (WO) . |
| WO 94/03631 | 2/1994 | (WO) . |
| 9417409 | 4/1994 | (WO) . |
| 9520160 | 7/1995 | (WO) . |
| WO 96/04547 | 2/1996 | (WO) . |
| WO 97/22000 | 6/1997 | (WO) . |

OTHER PUBLICATIONS

Chu et al., "Using Affinity Capillary Electrophoresis to Identify the Peptide in a Peptide Library that Binds Most Tightly to Vancomycin," J. Org. Chem. 58:648–652 (1993) No month available.

Chu et al., "Using Affinity Capillary Electrophoresis To Determine Binding Stoichiometries of Protein–Ligand Interactions," Biochemistry 33:10616–10621 (1994) No month available.

Chu et al., "Affinity Capillary Electrophoresis," Acc. Chem. Res. 28:461–468 (1995). No month available.

Crothers, "Gel electrophoresis of protein–DNA complexes," Nature 325:464–465 (1987), No month available.

Ceglarek et al., "Studies of DNA–protein interactions by gel electrophoresis," Electrophoresis 10:360–365 (1989) No month available.

Chu et al, J. Med Chem. 35:2915–2917 (1997) No month available.

Yen–Ho Chu et al "Affinity Capillary Electophoresis–Mass Spectrometry for Screening Combinational Libraries", J. Am. Chem. Soc. vol. 118: 7827–7835 (1996) No month available.

Chu et al., "Free Solution Idenntification of Candidate Peptides from Combinatorial Libraries by Affinity Capillary Electrophoresis/Mass Spectrometry," J. Am. Chem. Soc. 117:5419–5420 (1995). No month available.

Fried et al., "Measurement of protein–DNA interaction parameters by electrophoresis mobility shift assay," Electrophoresis 10:366–376 (1989) . No month available.

Xian et al., "DNA–protein binding assays from a single sea urchin egg: A high–sensitivity capillary electrophoresis method," Proc. Natl. Acad. Sci. USA 93:86–90 (1996). No month available.

Heegaard et al., "Use of Capillary Zone Electrophoresis to Evaluate the Binding of Anionic Carbohydrates to Synthetic Peptides Derived from Human Serum Amyloid P Component," Anal. Chem. 64:2479–2482 (1992). No month available.

Wagner et al., "Use of Affinity Capillary Electrphoresis to Measure Binding Constants of Ligands to Proteins," J. Med. Chem. 35:2915–2917 (1992). No month available.

(List continued on next page.)

*Primary Examiner*—Jill Warden
*Assistant Examiner*—John S. Starsiak, Jr.
(74) *Attorney, Agent, or Firm*—Weingarten, Schurgin, Gagnebin & Hayes LLP

(57) ABSTRACT

This invention relates to a competitive-binding, capillary electrophoretic method of detecting new therapeutic regulatory (modulating) and diagnostic compounds in natural samples and other complex biological materials. The present method generally comprises mixing a preselected, detectable target with a sample of complex biological material to produce a first, sample/target mixture capillary electrophoresis apparatus. Subsequently, the first mixture is mixed with a pre-selected, tight-binding competitive ligand (TBCL), prior to produce a second, sample/target/TBCL mixture, for a predetermined optional incubation period sufficient to allow the TBCL to bind a pre-selected percentage of the available target in the absence of any other ligand. An aliquot of the second mixture is subsequently subjected to pre-optimized capillary electrophoresis, during which the migration of the target is monitored. The presence of a potential new compound is indicated by the increase in the peak area of the unbound target peak and/or decrease in the peak area of the TBCL/target complex peak. A capillary electrophoretic profile of the second mixture is produced, which may be compared to a reference standard. The reference standard typically comprises a capillary electrophoretic profile or migration pattern of the target when mixed with a TBCL in an absence of any other competing ligand under similar, pre-selected capillary electrophoretic conditions.

32 Claims, 11 Drawing Sheets

OTHER PUBLICATIONS

Shimura et al., "Affinity Probe Capillary Electrophoresis: Analysis of Recombinant Human Growth Hormone with a Fluorescent Labeled Antibody Fragment," Anal. Chem. 66:9–15 (1994). No month available.

Sun et al., "Enhanced albumin protein separations and protein–drug binding constant measurements using anti–inflammatory drugs as run buffer additives in affinity capillary electrophoresis," Journal of Chromatography 661:335–340 (1994). No month available.

Heegard, "Determination of antigen–antibody affinity of immuno–capillary electrophoresis," Journal of Chromatography 680:405–412 (1994). No month available.

Liu et al., "Affinity capillary electrophoresis applied to the studies of interactions of a member of heat shock protein family with an immunosuppresant," Journal of Chromatography 680:395–403 (1994). No month available.

Pritchett et al., "Capillary Electrophoresis–Based Immunoassays," Bio/Technology 13:1449–1450 (1995) . No month available.

Koutny et al., "Microchip Electrophoretic Immunoassay for Serum Cortisol," Anal. Chem. 68:18–22 (1996). No month available.

* cited by examiner

CAPILLARY ELECTROPHORETIC METHODS TO DETECT NEW BIOLOGICALLY ACTIVE COMPOUNDS IN COMPLEX BIOLOGICAL MATERIAL

CROSS-REFERENCE TO RELATED APPLICATION(S)

This application claims the benefit of Provisional Application No. 60/069,943, filed on Dec. 17, 1997, herein incorporated by reference.

FIELD OF THE INVENTION

This invention relates to screening complex biological material for new biologically active compounds, and in particular, to using capillary electrophoresis for such screening.

BACKGROUND OF THE INVENTION

Developing screens to identify new biologically active compounds can present unique and difficult challenges, especially when screening naturally occurring complex biological materials (sometimes referred to as "natural samples" or "natural products"), various biological preparations, chemical mixtures, and other complex materials. Major problems include low concentrations of active compounds, unknown components that can interfere with screening agents, and isolation of the new compound once a positive sample is obtained. Despite these obstacles, the pharmaceutical industry still maintains a strong interest in the screening of complex mixtures. For example, it is widely recognized that nature provides a virtually endless supply of new chemical structures that are often difficult or impossible to synthesize in a cost-effective manner. Most natural products have some bio-activity, and historically, natural products and their analogs have been the most successful source of therapeutic compounds.

Screening technologies for therapeutic and other biologically active compounds fall into two broad categories: bioassays and mechanism-based assays (Gordon et al., *J. Med. Chem.* 37:1386–1401, 1994).

Bioassays represent the oldest, and so far, most productive screening tool. Bioassays measure the effect of natural samples on the viability or metabolism of disease-related cell types such as bacteria, fungi, viruses, and tumor cells. For example, the β-lactam antibiotics (e.g., penicillins and cephalosporins) were discovered by testing microbial broths for bacterial growth inhibition in culture tests. Likewise, the antifungal compounds, nystatin and amphotericin B, were isolated from broths that inhibited yeast growth in culture tests. However, mainly due to the lack of specificity and sensitivity of bioassays, the more sophisticated mechanism-based assays have replaced most bioassays as primary screens.

Mechanism-based assays can be subdivided into three general categories: (1) recombinant cell-based assays, (2) enzymatic/biochemical assays, and (3) binding assays. Today's assays must satisfy the need for high throughput capacity, so they must be robust, simple, and amenable to automation in a parallel processing mode.

Recombinant, cell-based assays screen for a given, known functional response. Usually a target receptor, enzyme, or other protein is introduced into cultured cells by genetic engineering. Inhibition or induction of target activity is associated with an easily-measured response. For example, modifiers of transcription factors (TF) can be measured by fusing the TF's target DNA sequence (typically an enhancer or promoter region) to a luciferase (light-producing) gene. TF agonists result in transcription of the luciferase gene, and light is produced. If an antagonist is present, light is not produced. One advantage of cell-based assays over enzymatic and binding assays is that they may provide more physiologically appropriate leads, because intact cells are used. On the other hand, cell-based screens can be very difficult to develop, slow and quite variable in their results (Janzen et al., *Society for Biomolecular Screening Meeting*, Nov. 7–10, 1995).

Enzymatic assays are cell-free screens that directly or indirectly test the effect of soluble compounds on the activity of purified target enzymes that are related to disease processes. For example, viral reverse transcriptase inhibitors can be screened by measuring the incorporation of radiolabeled thymidine into a growing DNA chain from a polyuridine RNA template. These assays can be very sensitive and are amenable to automation using microtiter plates. For natural product screening, however, unknown compounds in the samples can dramatically interfere with screening results, leading to unacceptably high levels of false negatives and false positives. For example, greater than 15% of aqueous extracts from terrestrial plants, cyanobacteria, marine invertebrates, and algae exhibit positive activity in screens for anti-HIV compounds, due to interfering compounds such as plant tannins (Cardellina et al., *J. Nat. Prod.* 56:1123–1129, 1993).

Binding assays are particularly useful for screening soluble mixtures of biological or chemical materials for compounds that bind, and thus potentially modulate or inhibit, physiologically active target molecules. These assays have been major screening tools in the drug discovery efforts of pharmaceutical and biotechnology companies. In immobilized-target binding assays, the target molecule (usually a protein) can be affixed or tethered to a solid substrate such as the side of a microtiter well, beads, or chromatographic supports. If the target molecule is a receptor, it can be expressed on the membrane of a cell attached to the solid support. The samples are incubated with the immobilized targets, and bound ligands are detected, usually through an associated calorimetric or fluorescent reaction. Alternatively, the sample is mixed with a soluble-phase target that is captured using an anti-target antibody. Such binding assays are advantageous because they facilitate the washing and isolation of target-ligand complexes.

However, immobilized-target binding assays also suffer from several disadvantages, particularly as a method for screening natural biological samples for new active compounds. One problem is that the binding of multiple background compounds, if present in sufficient quantities, may produce a positive signal that is indistinguishable from that of a single potential therapeutic compound. Therefore, screening with immobilized-target binding assays often requires heavy washing or improved clean-up capability. Another general problem is that affixing target proteins to solid substrates often inactivates the protein or produces a functional change. This problem can be addressed to some extent by using recombinant DNA technology to insert an inert "handle" such as a peptide epitope into the target protein. The protein-ligand complex can then be isolated through the use of an antibody to this epitope. However, development of these modified targets is time-consuming and expensive.

One commonly used binding assay is the microtiter-format, enzyme-linked immunosorbent assay (ELISA). One disadvantage is that the target molecule, which is usually attached to the well wall, does not contact most of the soluble sample dispersed throughout the well. Therefore, greater reaction times are needed, although some improvements have been made through using reduced reaction volumes. Another problem is that an ELISA requires the development of specific monoclonal antibodies, a time-consuming and often unsuccessful process.

There remains a need for rapid and cost-effective screening tools for discovering new bioactive compounds and potential drugs that bond to essential molecules of key metabolic pathways. The present invention relates to an improved method of screening complex biological material for new active compounds using capillary electrophoresis.

SUMMARY OF THE INVENTION

This invention is directed to a method of screening a sample of complex biological material, for example a natural sample, for a candidate new biologically active compound, or a new source of a known biologically active compound, that binds to a selected target of interest, e.g., a molecule involved in a disease. This method is particularly advantageous in identifying a screening sample that contains, as candidate "hit compounds," unknown moderately-to-tightly binding ligands ("MTBL") and even weaker-binding compounds (as well as tight-binding ligards). "Moderate-to-tight binding" ligands (MTBL) and "weak-binding"ligands have faster off-rates (Koff) and higher dissociaton constants ($K_D$), and form target/ligand complexes that hold together for little or none of a capillary electrophoretic run, i.e., target/ligand complexes that are unstable and fall apart quickly before reaching detector. In contrast, tight-binding ligands have lower dissociation constants and slow off-rates, forming target/ligand complexes that remain bound as they migrate past a detector during capillary electrophoresis. Typically, but not always, ligands of a particular binding strength have the respective characteristics shown in Table 1.

TABLE 1

| Ligand | Approx. $K_D$ range | Approx. $K_{off}$ range | Functional Definition |
|---|---|---|---|
| Tight-binding | <10 nM | <0.01 ($s^{-1}$) | Target/Ligand complex holds together at least until the detector |
| Moderate-to-tight-binding (MTBL) | 10 nM–10 $\mu$M | 0.01–1.0 ($s^{-1}$) | Target/Ligand complex dissociates within 5% of the distance to detector |
| Weak-binding | >10 $\mu$M | >1.0 ($s^{-1}$) | Target/Ligand complex dissociates within 5% of the distance to detector |

The method of the invention thus represents an improvement over other capillary electrophoretic analytical and/or screening methods that detect only compounds having a high affinity for a target of interest. This method advantageously enables the discovery, from complex biological material, of a wide scope of biologically active compounds with potential therapeutic, diagnostic, herbicidal, insecticidal, agricultural and/or veterinary applications.

The method uses a competitive binding and capillary electrophoresis ("CE") technique that combines a fractionation step with a solution-based affinity assay to discover new target-binding compounds, e.g., potential new regulatory molecules, drugs, or diagnostic compounds, from a variety of source materials. The competitive CE screening method of the invention overcomes major problems associated with current pharmaceutical screens such as poor detection levels (i.e., low sensitivity) and high false-positive hit rates caused by interfering compounds. Furthermore, the method of the invention is capable of identifying samples having target-specific, regulatory or other activity, which would previously have been undetected using other screening methods.

In the method of the invention, components of complex biological material, e.g., from natural samples or synthetic mixtures, are simultaneously fractionated and screened for compounds that are found to compete with a pre-selected, known ligand in binding to a specific target molecule of interest sometimes referred to as ("TG"). When isolated, such newly identified ligands are lead candidates for potential therapeutic, regulatory or diagnostic compounds. This assay system requires very small amounts of sample material and reagents, and utilizes a highly specific, solution-based affinity assay, thus facilitating the identification of a true positive sample while minimizing interference from background components.

In general, in order to practice the method of the invention for screening complex biological material for new active compounds, one must select a detectable target molecule of interest; select a known, tight-binding competitive ligand ("TBCL") that tightly binds to the chosen target so as to alter its capillary electrophoretic migration a pattern; and determine the "optimal incubation time" needed for a predetermined quantity of the TBCL to bind to or interact with a predetermined quantity of the target detectably. Preferably, but not necessarily, the TBCL concentration and incubation time used suffices to allow the TBCL to bind substantially all (e.g., 90–99%) of the available target molecules provided within the predetermined incubation time period. At a minimum, enough of the TBCL should be incubated with the target for enough time to allow at least 10% of the total target to form a stable complex having a detectably different migration pattern from that of the unbound target.

The screening method comprises providing a predetermined quantity of the target; providing a complex biological material sample to be screened; mixing the sample with the predetermined quantity of the target and waiting for a time period sufficient for any new ligand or hit compound in the sample to bind to the target, to produce a first sample/target mixture; subsequently, combining that first mixture with a predetermined quantity of the TBCL (to produce a second mixture) and waiting for the predetermined optimal incubation time; injecting an aliquot of the second mixture (of natural sample, target, and TBCL) into a capillary electrophoresis apparatus; subjecting the aliquot of the second mixture to capillary electrophoresis (CE); and tracking the migration of the detectable target molecule upon electrophoresis. Preferably, the method also includes comparing the migration and peak area of the detectable target in the second mixture, upon CE, to a "reference standard" (as discussed in the Detailed Description).

The TBCL must be "tight-binding" in that it forms a stable complex with the target molecule, which means that it does not appreciably dissociate during the CE run. The complex should hold together at least until it reaches the detection point of the CE run. Preferably, the TBCL has a low dissociation constantly, a $K_D$ of less than 10 nM, and a slow off-rate, a $K_{off}$ of less than $0.01(5^{-1})$. The CE run is typically about 0.5–10 minutes, or less if using a very short capillary. The target/TBCL complex must have a different CE migration time from that of the unbound TG. Since CE migration depends on an analyte's overall charge-to-mass ratio, the TBCL ideally should, under CE running buffer conditions, be charged (naturally or by modification) or have a significantly higher molecular weight ("MW") than the target (naturally or by modification) or at least change the charge-to-mass ratio of the target once bound. The bound target/TBCL complex should have a different charge-to-mass ratio from that of the unbound target, thereby achieving the complex's different migration pattern.

Any weak or moderate-binding compound present in the natural sample that binds to or interacts with the TBCL-binding site(s) of the target molecule during the first incubation step is likely to interfere with target/TBCL complex formation during the second incubation step. Any such interference will be detectable during CE if there is an increase in the unbound TG peak. That is, one would track the CE mobility profile or migration pattern of the detectable target after contact with, first, a natural sample and, subsequently, the TBCL. That migration pattern of the screened sample would be compared to, e.g., the migration pattern of the detectable target in the presence of the TBCL alone (absent a natural sample). The presence of a MTBL or weak-binding ligand would result in a reduced TG/TBCL peak and an increased unbound TG peak.

Ideally, both the unbound target and the bound target/TBCL complex appear as distinct peaks during CE. An increase in or re-appearance of the unbound target's migration peak, would signify the presence of a weakly to moderately target-binding ligand (MTBL), in the natural sample, which dissociates from the target during the early stages of CE. The unbound target is not able to bind the TBCL once the CE run has started because they are separated from each other due to differences in their mobilities. If a peak representing the bound target/TBCL complex is known to be detectable during CE, its absence or decrease (within the migration pattern of a screened sample/target/known ligand mixture), signifies the presence of a potential hit compound. Alternatively, the appearance of some other, new peak signifies the presence, in the sample, of a tight-binding unknown hit compound that has changed the overall charge-to mass ratio of the target once bound and that may or may not compete with the TBCL.

In the preferred method, both the unbound target and the TBCL/target complex are detected in the CE process. However, to practice the method successfully, it is sufficient to detect only one of these two components in the CE process.

For example, it is possible that the unbound target is not detected (i.e, does not give an "unbound target" peak), because it has a neutral charge or opposite charge to the polarity of migration, or it adsorbs to the capillary wall due to hydrophobic CE or ionic interactions. Upon binding the TBCL, however, the bound target may have different physical properties that enable it to be detected in the CE process. For example, the TBCL, upon binding the target, may provide a suitable charge on the target so that the target/TBCL complex migrates in the capillary and shows a distinct peak at a detection point. Alternatively, binding of the TBCL may change the conformation of the target so that it no longer adsorbs to the capillary wall and the target TBCL complex becomes detectable and serves as a reference standard (in the absence of any other ligand or hit compound). Where the unbound target does not give a distinct CE peak but a target/TBCL complex peak is visible, a decrease in the relative peak area of the target/TBCL complex peak indicates the presence of a hit compound that is a moderate-to-tight binding ligand (MTBL). This is because the presence of a hit compound, bound to the target from the first pre-capillary incubation step (incubatory the target and sample) prevented some of the TBCL from binding during the short, second pre-capillary incubation step (incubating the target, sample, and TBCL).

In another case, the unbound target may be detected as a CE peak but the target/TBCL complex may not. This can occur for similar reasons as described above for the case where the target/TBCL complex was detected by CE but the unbound target was not. In other words, binding of the TBCL may alter the physical properties of the target by changing its overall charge or adsorption properties such that the target/TBCL complex does not produce a CE peak. In this case, the presence of a moderate-to-tight binding hit compound is indicated by an increase in the relative peak area of the unbound target, compared to the case of a sample without a hit compound. This is because the presence of a hit compound, bound to the target from the first pre-capillary incubation step (incubatory the target and sample) prevented some of the TBCL from binding during the short second pre-capillary incubation step.

Any ligand or hit compound detected in a sample of complex biological material to compete with the TBCL in binding to the target molecule, is a lead candidate as a regulatory, therapeutic, or diagnostic compound. Once detected, a ligand newly determined to bind to the target molecule may be isolated from the complex biological material and be tested for, e.g., its therapeutic efficacy and pharmacokinetic properties.

With the use of fluorescent dye-conjugated molecules and laser-induced fluorescence, the method of the invention provides the ability to detect MTBL concentrations, directly in the sample, in the picomolar to low nanomolar range. This sensitivity is substantially greater than the high nanomolar to micromolar concentrations that are the limit in most current screening methods. In addition, capillary washing and replacement of buffer in a capillary electrophoresis system are rapid, allowing higher throughput of complex biological material samples than is possible with standard screening procedures based on affinity chromatography.

The method of the invention will permit the rapid detection of potentially useful, new or previously unidentified molecules in natural samples and other materials that are not detectable by standard screens due to low concentrations of these potential hit compounds and/or the presence of interfering compounds. The small scale of CE has major advantages in that the quantity of rare or potentially hazardous assay components used (e.g., the screening sample, the target molecule, the buffers or other reagents) can be reduced considerably.

The method of the invention will accommodate high-throughput screening of complex biological samples and be suitable for automation by employing robotics, multiple capillaries or multiple channels on microfabricated devices, and/or several target molecules per channel or capillary. In some cases, particularly when tight-binding hit compounds are detected, on-line structural information of lead candidates may be ascertained by coupling an analytical device such as a mass spectrometer or nuclear magnetic resonance apparatus, to the CE capillary or channel.

As well, the competitive CE screening method of the invention may be used in conjunction with separation, binding, purification and/or isolation techniques well-known in the art (such as, e.g., affinity chromatography), to identify and isolate hit compounds detected by the present screening method.

BRIEF DESCRIPTION OF THE DRAWINGS

Other features and advantages of the invention will be apparent from the following description of the preferred embodiments thereof, taken in conjunction with the accompanying drawings in which.

DETAILED DESCRIPTION OF THE INVENTION

Figure 1A:
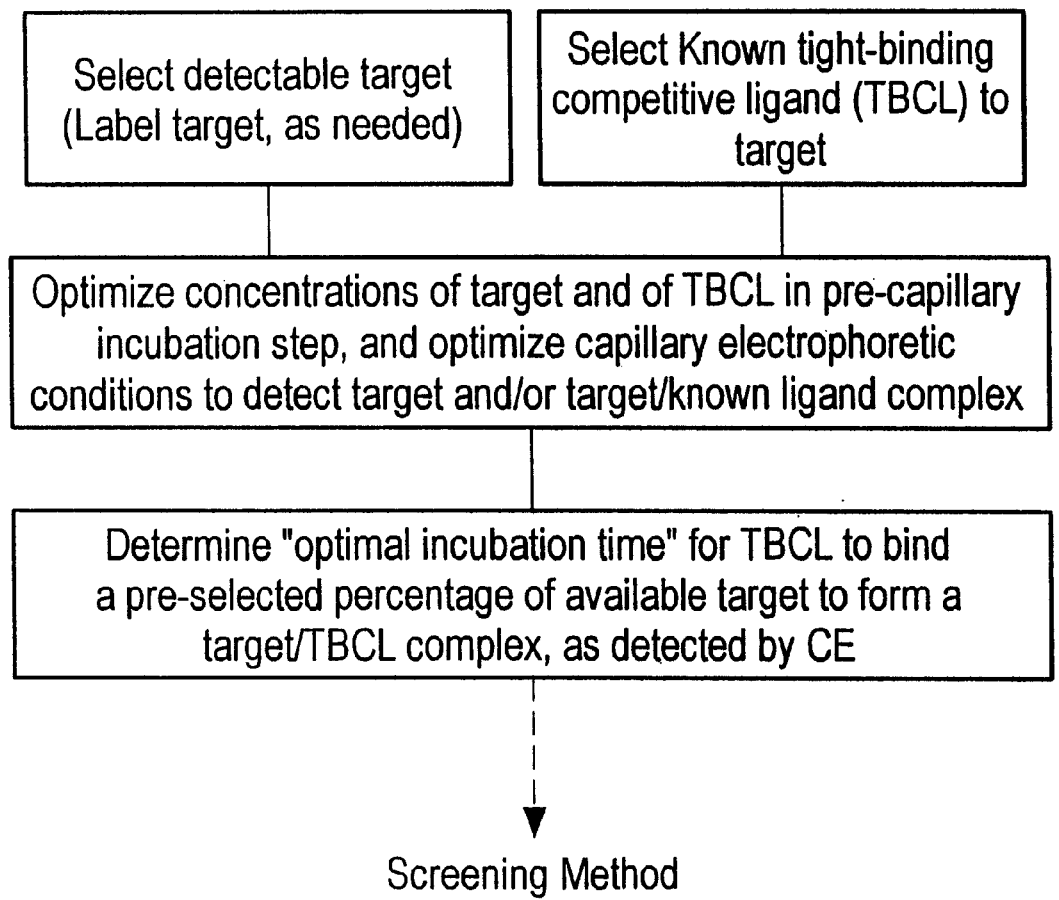
FIG. 1 shows (A) a flowchart of the optimization steps to be pursued prior to carrying out the screening method of the invention; and (B) a flow chart of the steps of an embodiment of the screening method.

The screening method of the present invention, involving competitive binding and capillary electrophoresis, involves at least three components: a known target molecule (sometimes called "TG", or "LTG" for a labelled target), a known, tight-binding competitive ligand (hereinafter called "TBCL") to that target, and a sample source that may or may not contain a potentially new or previously unidentified ligand (or a known ligand from a new source) that can compete with the TBCL in binding to the target but is weak enough that the target/unidentified ligand does not hold together during the CE run. The TBCL must alter the CE or migration pattern profile of the TG once it is bound. Typically, the sample source is a complex biological material, as defined later, especially a natural sample. The screening method allows one to identify samples that contain candidate new or unidentified ligands to the selected target of interest. In particular, it can find new or unidentified ligands that form complexes with the TG that are not stable during the CE run. Any new or previously unidentified, competitive, target-binding ligand identified to exist within the sample is a potential, therapeutically or biologically active compound suitable for modulating, inhibiting, or otherwise regulating the selected target. The compound may alternatively be useful for diagnostic purposes.

The optimization steps (discussed later) for the conditions of the screening method are depicted in a flowchart presented in FIG. 1A. The screening method is shown in FIG. 1B. Referring to FIG. 1B, the competitive binding, capillary electrophoretic screening method of the invention generally comprises, in the order given: (a) mixing and incubating the target with a sample to be screened, to produce a first, sample/target mixture, prior to capillary electrophoresis (b) subsequently, mixing the first mixture with a known, tight-binding, competitive ligand (TBCL) to the target, to produce a second, sample/target/TBCL mixture, and incubating for a predetermined, optimal incubation time (discussed later), also prior to capillary electrophoresis; (c) injecting an aliquot of the second mixture into the running buffer in a capillary electrophoresis apparatus and subjecting it to capillary electrophoresis; (d) tracking migration of the target during capillary electrophoresis and producing a capillary electrophoretic profile of the second mixture; and (e) comparing the second mixture's capillary electrophoretic profile with a "reference standard" comprising a capillary electrophoretic profile of the target when mixed with and bound to the TBCL in the absence of any competing ligand.

More specifically, the method of the invention involves first mixing and incubating the target and the complex biological sample for sufficient time to allow binding between the target and any unknown ligand i.e., hit compound, within that sample. This first incubation time is typically within 1–60 minutes. Subsequently, this first, target/natural sample mixture is mixed with a predetermined concentration of the TBCL, and then incubated in a second incubation step, for an "optimal incubation time" that has been predetermined in a separate optimization process (discussed later). The TBCL and TG concentration and the optimal incubation time of the natural sample/target mixture with the TBCL will have been predetermined during an optimization process separate from the actual screening method, as discussed later in greater detail with reference to FIG. 1A.

The two mixing steps of the screening method are performed in solution, generally with the target, natural sample, and TBCL each dissolved in a suitable, pH-adjusted buffer solution that may include buffer agents or other compounds, as needed to optimize target-binding (hereinafter called "sample buffer") After the second mixing/incubation step, a sample of the target/natural sample/TBCL mixture is injected into a capillary electrophoresis apparatus filled with a "running or background buffer," usually a pH-adjusted solution optionally containing buffer agents or other compounds, as needed, to optimize capillary electrophoresis of the selected target and the target/TBCL complex. The running and sample buffers may be the same buffer solution or different buffers and are discussed further in the optimization section.

One determines the presence of a potential, target-binding hit compound in the screened sample by comparing the CE profile of the sample/target/TBCL mixture with that of a "reference standard." The "reference standard" for the screening method comprises one or more of the following. The reference standard may be the migration time or the peak area of the target/TBCL complex peak and any unbound target in the presence of the TBCL during CE.

As well, the reference may be the known CE migration time of at least one independent compound that does not interfere with the target-ligand binding reaction and that is detectable during the CE run. An advantageous embodiment of the method may use as the reference, independent markers whose migration times are known to flank that of the target, so as to have a marker peak at about the beginning and the end of each CE run of a target-containing CE sample. An especially advantageous embodiment would include the combined use of several of the above-mentioned reference standards. This would be very advantageous when identifying new peaks that arise due to the presence of tight-binding hits that alter the target's migration.

For example, where the target/TBCL complex has a detectable peak distinct from the unbound target peak, the reference standard may be the migration and peak area of the target/TBCL complex as well as any remaining unbound target compared to the peak area of the target when complexed to the TBCL. The relative peak areas of the unbound target and of the complex during CE, in the absence of a hit compound serve as internal, negative controls. An increase in the unbound TG and decrease in the target/TBCL peak indicates the presence of a hit compound.

One may use the results of the present screening method to identify the samples of complex biological material that contain a hit compound responsible for producing a capillary electrophoretic profile (of target, natural sample, and TBCL) different from the mobility profile of the target when mixed with the TBCL alone. Having identified which natural samples have at least one unknown hit compound that can bind to one's target of interest, one can then use any of many known separation, fractionation, purification and extraction techniques, and/or affinity, binding, enzymatic or other functional assays to isolate from the sample, the active hit compound detected during the competitive CE screening assay of the invention. The isolation steps can be monitored by using the CE screening assay (activity-guided isolation) as described later.

Sample for Screening

Any pure, partially pure, or impure sample that contains complex biological material is considered an appropriate sample to be analyzed by the method of the invention. "Complex biological material" is intended to include any mixture of compounds that may contain compounds that are potentially useful in a biological system, e.g., whether human, other mammalian, or agricultural. For example, large chemical libraries are frequently generated by combinatorial chemistry to enable investigators to screen extremely large numbers of chemical compounds for potential therapeutic or diagnostic purposes. These libraries can be, in essence, modified biological scaffolds and could be screened advantageously by the method of the invention. Particularly suitable are natural samples, including but not limited to: extracts of terrestrial and marine plants, cells from higher animals including humans, eubacteria, actinomycetes and other bacteria, extracts from non-recombinant or recombinant organisms, microbial fermentation broths, both filamentous and non-filamentous fungi, protozoa, algae, archaebacteria, worms, insects, marine organisms, sponges, corals, crustaceans, viruses, phages, tissues, organs, blood, soil, sea water, water from a fresh-water body (e.g. lake or river), humus, detritus, manure, mud, and sewage or partially pure fractions from isolation procedures performed on any of these samples (e.g., HPLC fractions).

The natural sample may be one that is harvested from the environment and/or cultured under suitable environmental conditions (growth medium, temperature, humidity). Preferably, the harvested sample is simply diluted to the extent necessary to practice the method of the invention. However, if necessary, the sample material can be treated by any combination of standard processes used by those skilled in the field to prepare the sample for analysis. For example, the crude sample may be subjected to a preliminary treatment such as freeze-thawing, homogenization, sonication, heating or microwave extraction to break down cell walls. The sample could be heated at, e.g., 50° C. for 10 minutes to inactivate destructive enzymes. Non-specific proteins may be added to prevent destruction of proteinaceous targets by heat-resistant proteases. Extraction of cells or culture media with various solvents—such as ethyl acetate, dimethylsulfoxide, ethanol, methanol, ether or water—can be carried out, followed by filtration to remove particulate matter and/or high molecular-weight compounds. The natural sample may also be fractionated by centrifugation, sequential extractions, high pressure-liquid chromatography, thin-layer chromatography, countercurrent chromatography, and/or other chromatography techniques. Various fractions of a positive sample may be tested to help guide the detection and isolation of active compounds by the method of the invention.

Finally, the sample may be diluted in aqueous or non-aqueous solution, which may contain salts and buffers such as sodium chloride, sodium citrate or Good's biological buffers. For most samples, the dilution step is required and preferably is the only treatment. However, dilution can also be performed as a final procedure after one or more of the preceding steps. A dilution of about 1:10 to about 1:20 (vol./vol.) of the original complex biological/material sample is usually preferred to achieve reproducible results in the screening method of the invention. Other dilution factors may be desirable.

Target

To practice the screening method of the invention, one selects a desired target compound, and obtains a sample of the target. Due to the high resolving power of capillary electrophoresis, the target sample may be purified, partially purified, or even unpurified (e.g., as in a bacterial extract), as long as the target and/or TBCL/target complex (preferably both) give(s) a discernible CE peak. Any molecule that is implicated in a disease process is a potential target. Furthermore, the potential target may be any compound useful in diagnosing a specific condition. Additionally, other categories of target molecules can be contemplated. For example, in the agricultural arena, the target could be a molecule representing an essential function of an insect pest. The target can be any known molecule having a TBCL. Examples of target molecules that may be used in the screening method of the invention include: proteins, nucleic acids, carbohydrates, and other compounds. Some examples of therapeutic target molecules are included in the following table:

| Molecular Target | Associated Disease(s) |
| --- | --- |
| HIV reverse transcriptase | AIDS |
| HIV protease | AIDS |
| Carbonic anhydrase | Glaucoma |
| Tubulin | Cancer |
| Thrombin | Blood clots |
| HMG-CoA reductase | High cholesterol |
| Elastase | Emphysema, Rheumatoid arthritis |
| Cyclooxygenase | Inflammation |
| p56, p59 tyrosine kinases | Cancer |
| Topoisomerases | Cancer |

Other examples of appropriate molecular targets include DNA or RNA (used to search for nucleic acid-binding proteins, transcription factors, etc.) ribosomes, cell membrane proteins, growth factors, cell messengers, telomerases, elastin, virulence factors, antibodies, replicases, other protein kinases, transcription factors, repair enzymes, stress proteins, uncharacterized disease-related genes and/or their RNA and protein products, uncharacterized disease-related regulatory DNA or RNA sequences, lectins, hormones, metabolic enzymes, proteases and toxins. The definition also includes any subcomponent of the listed molecules such as protein subunits, active peptide domains of therapeutic proteins, and active regions of small molecules. The molecule may be chemically, enzymatically, or recombinantly altered to improve its electrophoretic properties (e.g., deglycosylated), or subjected to fluorophore or polyion addition to facilitate its separation and/or detection during CE.

Depending on the nature of the target, it may be obtained from a variety of sources, such as a natural source; a cloned source, e.g., cDNA library, cloned proteins or peptides); a substantially pure source, e.g., purified protein sample, purified protein from a cloned cell extract, a protein of a specific molecular weight); or even an unpurified source (e.g., cloned bacterial or fungal extract, tissue or cell sample, or plant extract).

The target should be detectable during capillary electrophoresis, as unbound target and/or as target complexed with a TBCL, preferably both cases. For instance, it may be detectable by observation of its ultraviolet (UV) or other light absorbance properties, or its fluorescence properties. Preferably, one may label the target with a detectable tag, such as a fluorescent or other dye tag, a radio-label, a chemical tag, or other marker. For example, a fluorescently labeled target may be detected by ultraviolet light absorption detection (typically having a micromolar detection limit) or, more preferably, by laser-induced fluorescence detection (typically having a picomolar to low nanomolar detection limit). An additional advantage of a fluorescent tag is the selectivity provided, particularly in complex samples that may have many UV-absorbing compounds present. The need for a detectable tag, and the type used, will depend on the nature of the target molecule.

Proteins and peptides may be labeled by, e.g., amino labeling of lysine residues or sulfhydryl labeling of cysteine residues. Nucleic acid species and polynucleotides may be labeled by incorporating a labeled nucleotide in an in vitro synthesis reaction. Fluorescent tags, of which many are known, are particularly advantageous labels. Methods of labeling various targets are well-known in the art, and examples are given later in the description of detection optimization steps.

A substantially pure sample of the detectable target is preferably used in the competitive binding and capillary electrophoresis screening method of the invention. One may purify the target, especially one that has been fluorescently labeled, by preparative capillary electrophoresis, high-pressure liquid chromatography (HPLC), or other chromatographic methods.

If desired, one may confirm that a modified target, e.g., a fluorescently labeled target, retains its functional activity. That is, one can confirm that the labeled target retains a functionally active site by using any available, well-established functional or binding assay whose result depends on a functionally active target.

Known, Tight-binding Competitive Ligand

A known, tight-binding competitive ligand (TBCL) known to have a high binding affinity for the target is selected for use in the present screening method. The TBCL is selected for its ability to alter the CE migration of the target when bound. "Tight-binding" means that when the TBCL binds to the target, the resulting target/TBCL complex remains stable past the detection point of the CE run. The complex's stability can be increased by several methods, including lowering the CE temperature or modifying the CE buffer pH or salt composition. For weaker TBCL's, shorter capillaries may be used, or the sample can be pushed closer to the detection window immediately after injection (prior to applying voltage to the CE capillary) to give less time for the weaker TBCL to dissociate from the target. The TBCL is preferably charged although the only requirement is that it changes the overall charge-to-mass ratio of the target once bound. If the TBCL is naturally a neutral compound, one may chemically modify it to add a charge, as needed. Alternatively, the TBCL may have a significantly large mass compared to the target. In either case, the resulting target/TBCL complex should have a net charge-to-mass ratio that differs detectably from that of the target alone. During capillary electrophoresis, the complex would have a different electrophoretic profile from that of the unbound target itself.

More charge on the TBCL is usually desirable because it gives better separation from the unbound target peak. Also, a stronger binding TBCL is desirable because it may give a sharper complex peak.

The TBCL may be any of a wide variety of compounds. For instance, it may be selected from natural or synthetic compounds or drugs known to bind to the target of interest. Examples of TBCL's include the following: for human carbonic anhydrase II (HCA-II), dorzolamide; for thrombin, hirudin; for tubulin, colchicine or vinblastine; for general targets, antibodies to the target.

Capillary Electrothoresis Conditions for the Screening Assay

When preparing the present competitive binding and capillary electrophoresis screening method for a selected target and a TBCL to that target, one must determine the conditions that give the optimal detection of the target, alone and when bound to the TBCL. One must establish the conditions that produce distinguishable peak(s) for the unbound target and/or the target/TBCL complex. The optimal electrophoretic profile has at least either an unbound or a bound target peak that is about three times higher than a baseline representing background noise.

A typical CE system includes a separation capillary (having coated or uncoated inner wall), electrophoresis buffers supplying the inlet and outlet ends (and interior) of the capillary. The CE system generally needs no sieving or other interaction matrix.

The conditions used will be determined mainly by the characteristics of the target molecule including its overall charge, structural stability, functional activity, and detection potential under various buffer and electrophoretic conditions. They will also depend on the nature of the TBCL selected (such as the conditions under which it forms a stable complex with the target), as well as the type of material to be screened for a new hit compound binding to the target of interest. The particular conditions appropriate for a specific natural sample and specific target molecule can be determined by routine experimentation according to methods well known to those of ordinary skill in the art, particularly in view of the following considerations.

Optimization

Figure 1B:
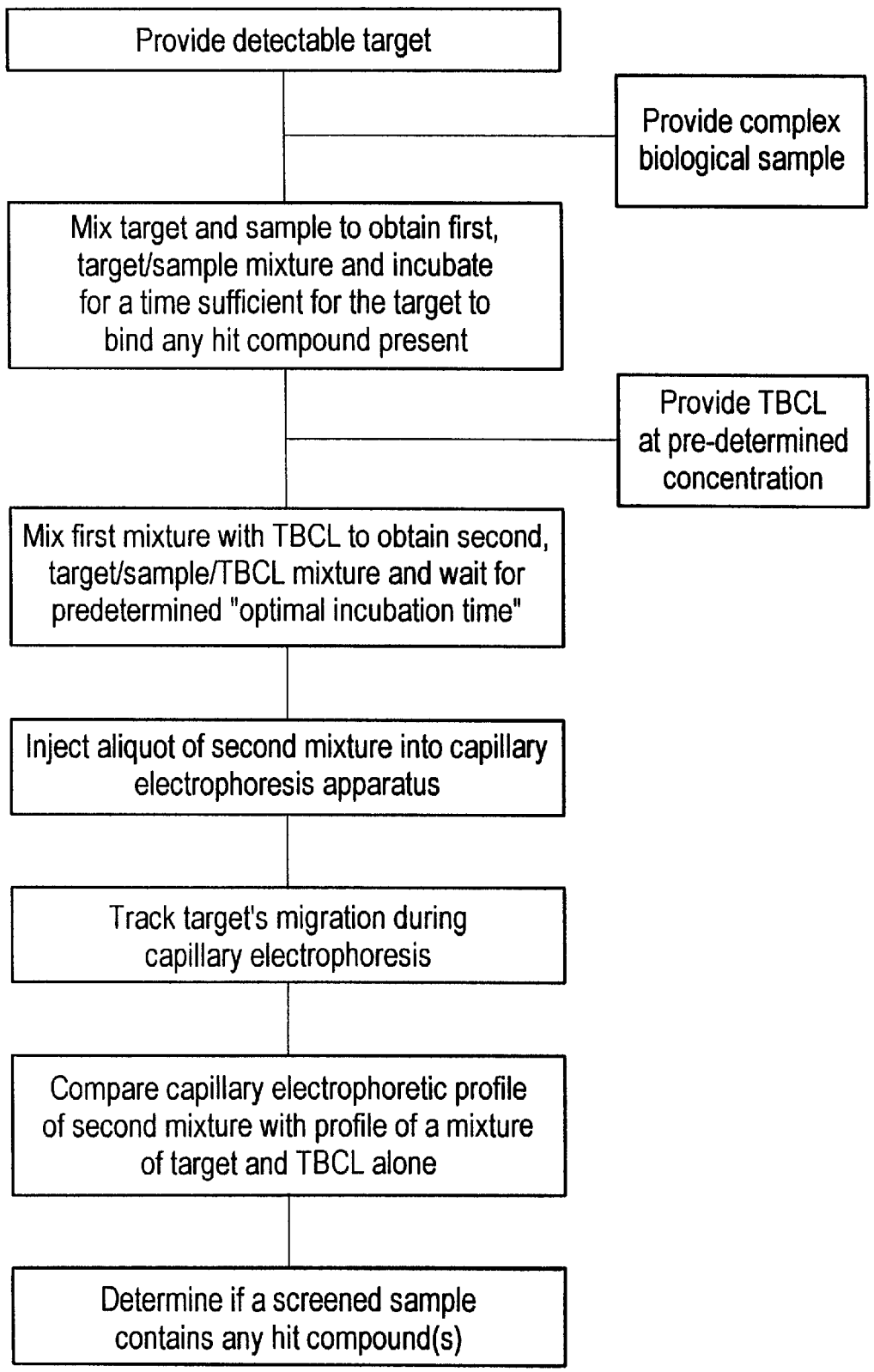

Prior to the performance of the screening assay itself, several optimization steps must be carried out, for the incubation of the detectable target of interest with the TBCL and for the capillary electrophoretic (CE) conditions, as shown in FIG. 1A. The optimization steps are designed to adapt the competitive binding and CE conditions for optimal CE detection of the target and target/TBCL complex selected for a given screening assay of the invention. One selects the target, labelling it as needed to ensure that it is detectable during CE, and the TBCL. One then optimizes the concentrations of target and TBCL to be incubated together before capillary electrophoresis. One then optimizes the CE conditions to detect the unbound target and/or the target/TBCL complex. Using the CE profiles from multiple target/TBCL incubation experiments, one then determines the optimal incubation time needed for the TBCL to bind to a pre-selected percentage of available target to form a target/TBCL complex. Specific optimizations are discussed below.

Optimization of capillary electrophoretic conditions for the screening method

1. Buffer condition optimization

The present screening method requires the use of at least one buffer, but may require two: (a) a sample buffer and (b) a running buffer. In most cases these buffers will be different but they may be the same buffer. The "sample buffer" is a pH-balanced solution for preparing samples of the target, the TBCL, or the natural sample to be screened for a hit compound that binds to the target. The "running buffer" is a pH-balanced solution used in the capillary electrophoresis apparatus. Examples of sample buffers and running buffers include Good's biological buffers (e.g., TES, CAPSO, etc.) or Tris based buffers.

One adjusts the sample and running buffers to each have a suitable pH for preserving the target's functional activity, e.g., binding activity, and allowing binding of the target to its TBCL. As well, the running buffer's pH value should be such as to produce suitable capillary electrophoretic profiles of the target alone and/or the target/TBCL complex. The running buffer should ideally allow the unbound target to produce a detectable peak when subjected to capillary electrophoresis, within a reasonable time period (e.g., preferably under 10 minutes). Each buffer solution may include appropriate additives, as needed. Suitable buffers are well-known in the art to one of ordinary skill.

2. Capillary optimization

Various capillary parameters may also be adjusted to allow optimal capillary electrophoresis conditions for a selected target molecule and its TBCL. Some capillary dimensions or factors that may be optimized include, but are not limited to: capillary size or diameter; capillary temperature; capillary length; inner coatings for the capillary, if necessary; and any capillary pretreatment, if necessary.

A preferred capillary inner diameter is within the range of about 10–500 microns, preferably within about 25–100 microns. The capillary length will depend on the amount of time needed for obtaining good capillary electrophoretic profiles of the selected target and/or the target/TBCL complex. Longer or narrower total capillary lengths can be used to improve resolution. However, longer capillaries also increase the time of the experiment, which may be detrimental to sample throughput. Longer capillaries may also increase any tendency of the TBCL to dissociate from the I.G. target, restricting the choice of the TBCL to only very tight binders, which may be difficult to obtain. Typically, a preferred capillary length is within a range of about 0.5 cm to about 1 meter, most preferably within about 0.5 cm to 40 cm. Optionally, the inner wall of the capillary may be coated with a polymer, a polymer blend, or other suitable material. The inner capillary coating may serve to minimize any electrostatic charge on the capillary wall and to diminish adsorption of a selected target, a selected TBCL, or the target/TBCL complex to the capillary wall. As well, the coating may also be pre-treated as needed. For instance, it may be pre-treated with a non-specific protein, such as bovine serum albumin (BSA), to help prevent target adsorption.

CE may also be carried out in capillaries in the form of open grooves or channels in a planar surface such as a fused silica or polymer microchip.

3. Detection optimization

The migration of the tracked target molecule is followed typically by the use of an on-column detector aligned with a small window etched into the capillary. Alternatively, it is possible to scan the entire capillary. It is also possible to perform a complete scan on individual peaks using a diode array spectrophotometer. Preferred detection methods use UV absorbance, UV or laser-induced fluorescence, and visible light absorbance. Other on-column detection methods may also be used. As well, one may use on-line detection instruments coupled with the capillary electrophoresis apparatus, which use radionuclide, fluorescence polarization, NMR, mass spectrometry, electrochemical detection and other methods.

The detection variable for direct detection can be absorbance at 210 or 280 nm for most proteins and 260 nm for nucleic acids. Indirect detection uses laser-induced (or other) emission of mainly visible wavelengths from dye-labeled target molecules which give high sensitivity. Preferred are fluorescently labeled molecules. Non-limiting examples of fluorescent dyes include fluorescein, rhodamine, tetramethylrhodamine, Texas Red and ethidium bromide. it must be kept in mind, however, that these labels can influence the overall charge on the target molecule and may affect its binding capability. Examples of UV sources and lasers include: deuterium, xenon and mercury lamps; argon, Ar/Kr, HeCd, HeNe, XeCl, KrF, nitrogen and solid state lasers. Some target molecules such as carbohydrates and small molecules, may require pre-capillary derivatization to be detected.

Prior to carrying out the screening method on a natural sample, one determines the most appropriate means of detecting the chosen target and/or target/TBCL complex during capillary electrophoresis; i.e., one determines a particular wavelength or other parameter at which the target and/or target/TBCL complex is optimally detectable.

4. Optimization of capillary electrophoresis conditions

The capillary electrophoresis process is adjusted to produce the optimal electrophoretic profiles for the unbound target and target/TBCL complex. Preferably, the profiles, when superimposed, will display at least two distinct peaks corresponding to the selected target molecule alone and to the target when bound to the selected TBCL (the target/TBCL complex).

Some electrophoretic parameters to be optimized include, but are not limited to: time, voltage, current and temperature. One can adjust the time or duration of the electrophoretic run so that it is possible to estimate when the target will be detected, alone or in complex with its TBCL, at a specific detection point in the capillary electrophoresis apparatus. The detection point may constitute at least one window in the capillary, at which is placed a detector. For instance, in the case of a fluorescently labeled target, there may be a fluorescence detector and an ultraviolet or laser light source to cause fluorescence. The capillary electrophoresis procedure may be set to run for up to 2 hours or even longer, as needed. Preferably, the duration of a CE run is set so that the target and/or target/TBCL peak(s) should be detected in less than ten minutes.

5. Target concentration optimization

The optimal target concentration is determined that, during capillary electrophoresis, ideally produces at least one detectable target peak having an amplitude preferably about 3 to 10 times above a baseline representing background noise (but the peak can be greater). Preferably, the unbound target is detectable. In determining the optimal target concentration, one typically performs a target concentration titration curve. To do so, one: (a) subjects target samples of different concentrations (but having the same injection volume) to capillary electrophoresis; (b) observes the size of detectable target peak that each concentration produces; (c) plots a curve of target concentration versus detection level (e.g., fluorescence level); and (d) selects the target concentration producing the electrophoretic peak size desired. In general, the lower the target concentration, the greater the sensitivity to binding ligands (hit compounds); however, lower target concentrations may result in adsorption problems. Therefore, the predetermined target concentration must take these factors into account.

It is possible that some target molecules may not be detected in an unbound state because they have a neutral charge or one opposite to the polarity of electrophoresis, or because they adsorb to the capillary wall during electrophoresis. In this case, one must select a TBCL that upon binding, changes the target's charge and/or conformation so as to make the bound target (i.e., the target/TBCL complex) detectable during CE, and then choose the optimal target concentration by doing a titration curve using the bound target/TBCL complex as the detectable peak.

For protein targets, a preferred concentration is typically in the range of about 1–100 nM for fluorescence detection, or about 0.5–100 μM for detection by UV absorption. More preferably, a fluorescently labeled protein target has a concentration of about 1–5 nM.

Optimization of conditions for pre-capillary incubation of target with known, tight-binding ligand To establish a successful screening method to detect a new active hit compound that binds to a selected target, one must first establish the optimal conditions for incubating the selected target with a TBCL so as to permit a desired amount of binding of the target and TBCL in the absence of any other ligand. Prior to the screening method, one predetermines the optimal concentrations or amounts of TBCL and target to use in that method. One also must determine an "optimal incubation time" for the target and TBCL mixture, as well as other reaction parameters not already determined (e.g., capillary length or reaction temperature), which will allow the desired percentage binding of the available target to the TBCL.

1. Determining the concentration of known tight-binding competitive ligand (TBCL) to use.

One selects a known, tight-binding competitive ligard (TBCL) concentration that binds detectably to the target provided. When subjected to electrophoresis in an optimization process, the target/TBCL complex, preferably but not necessarily, gives a CE profile with a substantially diminished, unbound target peak and, a concurrent, separate peak representing the bound target/TBCL complex. Ideally, when two such peaks are observable, one wishes to incubate the TBCL with the target for sufficient time to produce a detectable change in the target's CE profile. It is preferred but not essential to use a TBCL concentration that shifts the target's migration pattern substantially completely (i.e., in the range of about 90–99% of available target) from the unbound target position to the bound complex position. If, for the target/TBCL mixture, only one peak (either the unbound target or the target/TBCL complex) is visible, then one selects a TBCL concentration that produces a selected amount of detectable change in the target's CE migration pattern compared to the migration pattern of the target alone. That amount of change may be selected to correspond to a desired percentage of target that complexes with the TBCL (e.g., 10%, 50% or 90–99%). One tries to avoid using an excess or saturating amount of TBCL, which would tend to out-compete any unknown hit ligand (from the screened sample) in binding to the target and thus make hits that are weaker or less concentrated than the TBCL undetectable during the screening (i.e., decrease assay sensitivity). When feasible, it is most desirable to choose a concentration of the TBCL that leaves a minimally detectable, unbound target peak during CE, to serve as a control or marker showing where that peak should be and to show that an excess amount of TBCL has not been used.

In determining the TBCL concentration to use, samples of the selected, detectable target (e.g., a fluorescently labeled target) are mixed with samples of TBCL, using a constant concentration of the target and different concentrations of the TBCL. The constant target concentration is established according to the target concentration optimization step outlined previously and is preferably one that produces an optimally detectable target peak during capillary electrophoresis (e.g., 1–5 nM for a fluorescently labeled protein target). The target and TBCL are then incubated for a period of time that allows equilibrium or near equilibrium conditions to be reached.

A sample of each mixture of the target and a different TBCL concentration is subjected to capillary electrophoresis. One then observes the capillary electrophoretic profile for each target/TBCL mixture. Preferably, at least two peaks should be observed, corresponding to the unbound target alone and to the bound target/TBCL complex. The relative sizes of each peak will depend on the amount of target that is bound or unbound. However, depending on the particular charge-to-mass ratio or conformation of the complex, one may or may not see either a complex peak or an unbound target peak. It is important to detect at least one of the peaks and any change to it. Ideally, one determines the lowest concentration of the TBCL needed to produce a pre-selected, detectable change in the target's electrophoretic peak(s). For instance, if the unbound target alone can be seen as an "unbound target peak" during CE, one may select a TBCL concentration that is twice the smallest concentration required to reduce the unbound target peak (e.g., by 90–99%), and that correspondingly shifts the target substantially over to the detectable target/TBCL complex peak.

Figure 2:
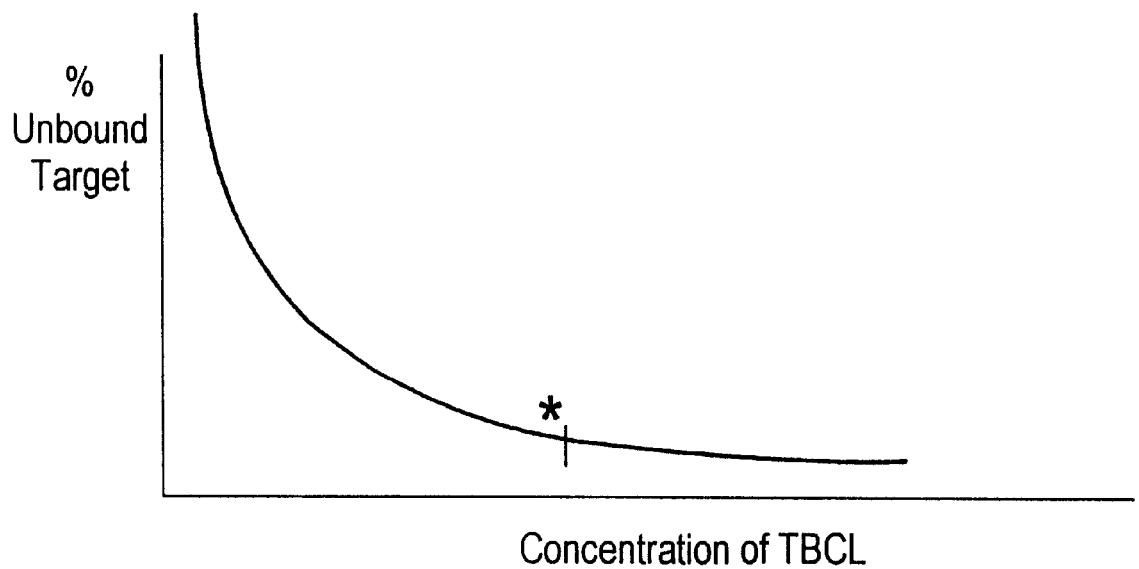
FIG. 2 is a titration curve plotting concentration of the known, TBCL against the percentage of unbound target remaining after incubating a predetermined concentration of target for a given time, with different concentrations of the TBCL.

In determining the lowest effective concentration of TBCL, one uses the results of the different capillary electrophoresis runs (of a constant concentration of the target with different concentrations of the TBCL) to plot a titration curve of TBCL concentration versus the percentage of target remaining either unbound or bound. Referring to FIG. 2, a titration curve is shown plotting the concentration of TBCL against the percentage (%) of unbound target remaining after incubating the predetermined concentration of target with different concentrations of the TBCL. The incubation time should be long enough to allow equilibrium or near equilibrium conditions to be reached, e.g., about 30 minutes for the Examples discussed later. The percentage of unbound target remaining after contact with the TBCL, can be calculated by, e.g., comparing the respective areas under the unbound target peak and the bound target/TBCL complex peak, within a single electrophoretic run of a sample of the target/TBCL mixture, as shown below:

$$\% \text{ unbound target} = \left[ \frac{(\text{Area of unbound target peak})}{(\text{Area of unbound peak}) + (\text{Area of bound complex peak})} \right] \times 100$$

Alternatively, one may just calculate the decrease in the unbound peak if the complex of target bound to the known competitive ligand is unobservable as a separate peak. Similarly, one may calculate the increase in the complex peak if the unbound target does not produce a distinct CE peak.

2. Time of pre-capillary incubation

An optimal time of incubation between the target and TBCL must be established and used, or the screening method may not detect unknown binding compounds that are weaker than the TBCL or at very low concentrations. That event becomes increasingly likely if the system is allowed to come to equilibrium with the TBCL because the TBCL may eventually replace most unknown hits bound to the target.

The optimal time of pre-capillary incubation of TG with TBCL is determined in the following way. The predetermined concentration of the TBCL is mixed together with the predetermined concentration of the target as determined in preceding sections. One then incubates samples of this mixture for different lengths of time. Subsequently, one subjects a sample from each experimental incubation time to capillary electrophoresis and compares the results from the different incubation times. From that comparison, one determines the optimal pre-capillary incubation time that is needed to allow the selected amount of binding between the predetermined amounts of target and TBCL (e.g., 10%, 50%, or 90–99% of available target). That is, the optimal time is the least or shortest amount of time one can use to incubate the target and TBCL together to produce the desired amount of detectable change in the capillary electrophoretic profile of the detectable target peak. If too much incubation time is used, the screening assay's sensitivity is greatly reduced. This least amount of incubation time is then used for the second incubation step of the screening method, in which a sample, target, and TBCL are incubated together. Ideally, when both the unbound target and the bound complex both produce detectable CE peaks, then it is most advantageous to use the shortest or least incubation time possible and the TBCL concentration that shifts substantially all (90–99%) of the unbound target peak to the bound complex peak. This least amount of incubation time is hereinafter referred to as the "optimal incubation time."

Figure 3:
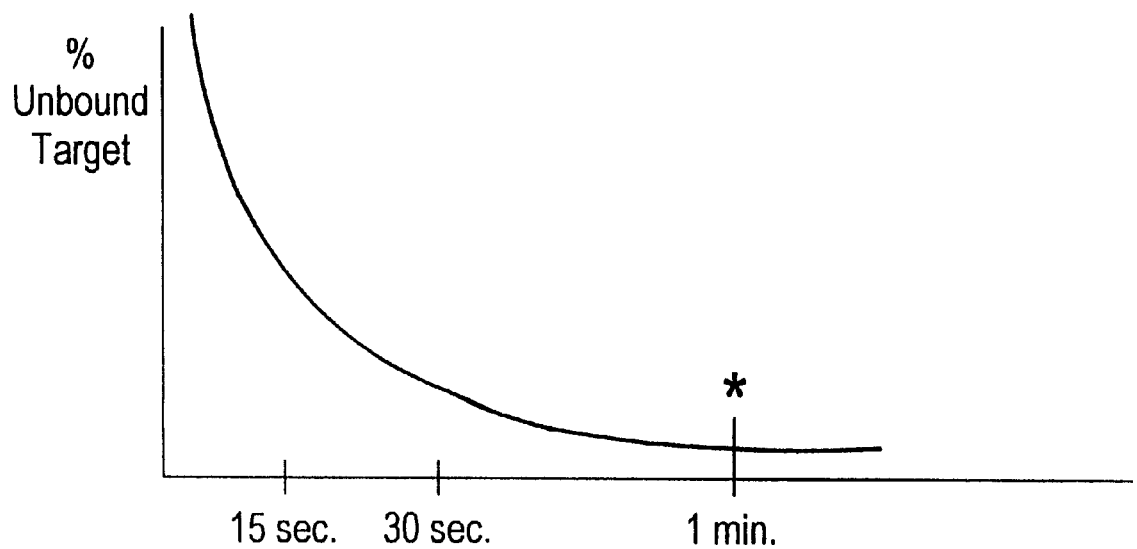
FIG. 3 shows a titration curve plotting different incubation times (of the TBCL with the target at predetermined concentrations), against the percentage of unbound target remaining after each incubation time period.

FIG. 3 shows a time course curve plotting percentage (%) of unbound target against different incubation times of the target with a set concentration of the TBCL, which is used to determine the optimal incubation time needed to allow the TBCL to bind to the desired percentage of target, in this case, substantially all available target molecules. For example, in this case, the optimal incubation time is quite short, approximately in a range of about 0.75 to 1 minute.

After completing the preceding optimization steps, one has determined the necessary parameters or criteria for performing the present screen to detect potential new active compounds that bind to, and possibly regulate, the target molecule of interest. One knows: (a) the best detectable target concentration to use; (b) the best TBCL concentration to use; (c) the optimal incubation time for incubating the detectable target with the TBCL (and with the natural sample, in the screening method); and (d) the best capillary electrophoresis conditions for a selected target and TBCL.

Validation of Screening Method with Known, Moderate-to-tight-binding Ligand (to Represent an Unknown Ligand or "Hit Compounds")

"Moderate-to-tight binding ligand" "MTBL" means that the ligand/target complex is relatively unstable and dissociates early-during the CE run. Thus, this complex cannot be detected as a separate, target/MTBL complex peak.

For a MTBL to be detectable, it must bind to the same site on the detectable target as the TBCL used in the screening assay. In a validation run, a MTBL is used to represent a test hit compound in a test run (e.g., a natural product hit in a natural sample), and is combined with the target in a longer, first pre-capillary incubation step (e.g., about 5–60 minutes). The MTBL binds to the target and will "protect" the binding site of the detectable target from binding the TBCL during the shorter, second pre-capillary incubation step, involving the MBTL/target/TBCL mixture, for the predetermined optimal incubation time (e.g., approximately 1 minute).

Ideally, subsequent capillary electrophoresis of an aliquot of the MTBL/target/TBCL mixture from the second pre-capillary incubation step will now exhibit two peaks, one corresponding to the target/TBCL complex formed and another corresponding to the unbound target, because not all the target could bind to the TBCL during the optimal incubation period due to the presence of the MTBL on the TBCL-binding site of the target.

Specifically, a sample spiked with the test MTBL or hit compound is mixed with a predetermined concentration of the detectable, e.g., fluorescently labeled, target. This first mixture is allowed to incubate, e.g., for at least 5–60 minutes, to allow enough time for binding of the target to the test hit compound to occur. The TBCL is then added at the predetermined concentration and mixed, and the resulting second, MTBL/target/TBCL mixture is incubated for the previously determined, optimal incubation time. Following the second incubation step, the sample is injected into a capillary electrophoresis apparatus and capillary electrophoresis is carried out. The percentage of unbound detectable target is then calculated with reference to the peaks appearing in the CE profile of the target mixed with only the TBCL. A larger unbound target peak indicates the presence of an MTBL.

The screening method may be calibrated by performing the validation assay with different MTBL concentrations and plotting the MTBL concentration versus the percentage of unbound detectable target.

Figure 9:
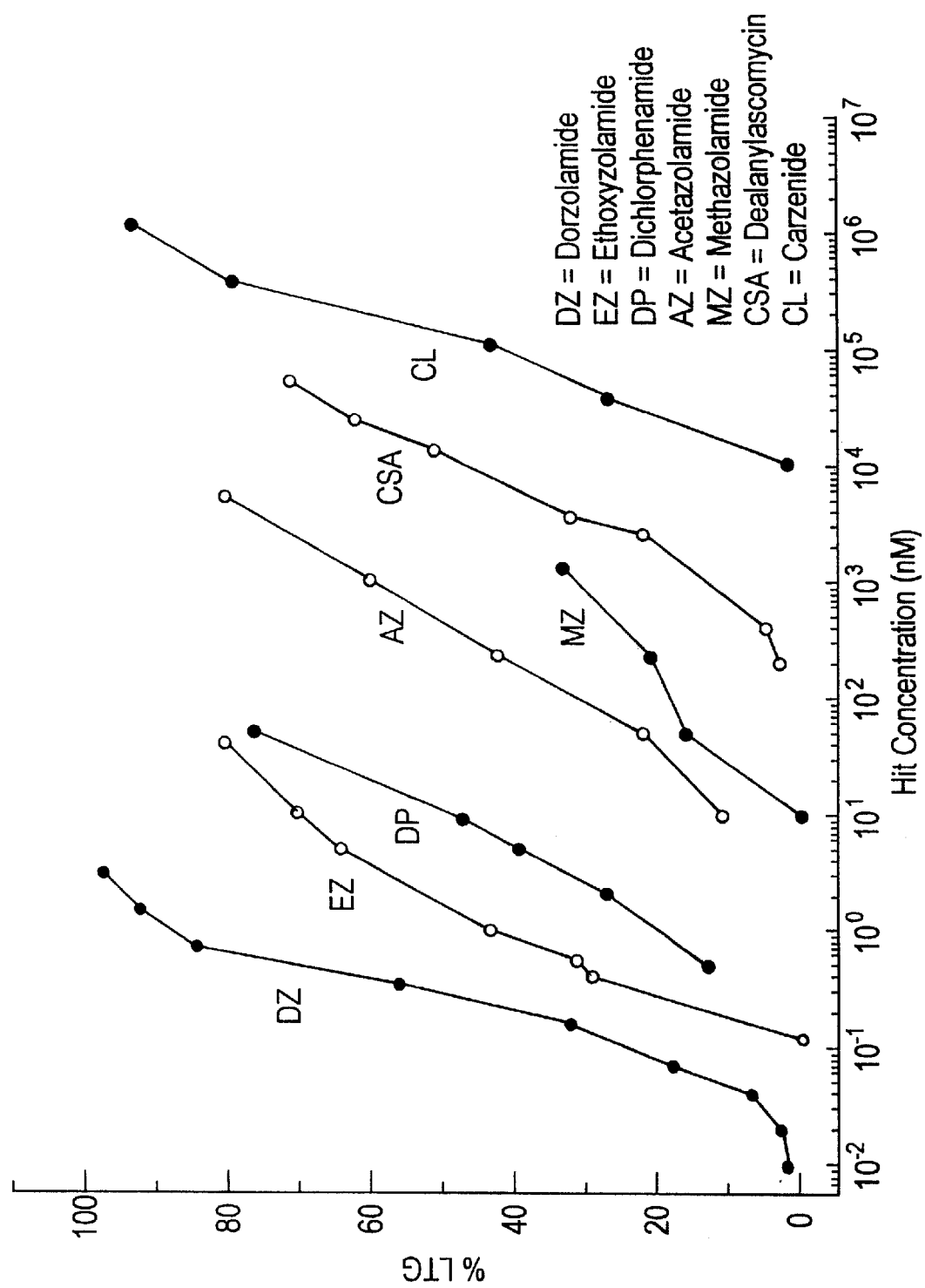
FIG. 9, shows "Hit" calibration curves plotting different concentrations of test hit compounds (HCA-II inhibitors) against the percentage of unbound target, (labeled HCA-II) (%LTG) remaining after incubation with a hit compound and then the TBCL (DZ).

FIG. 9 shows calibration curves of sample "hit compounds" that are MTBL (and also inhibitors) of a labeled target that is fluorescein-labeled human carbonic anhydrase II ("LTG"). The TBCL used in the example is dorzolamide ("DZ"). The calibration curves plot the percentage (%) of unbound LTG observed during CE, after incubating the predetermined concentration of LTG, first with different concentrations of the sample hit compounds, and subsequently with the predetermined concentration of DZ for the optimal incubation time. The percentage of unbound target is calculated as follows:

$$\% \ LTG = \left[ \frac{(\text{Area of unbound} LTG \text{ peak})}{(\text{Area of unbound } LTG \text{ peak}) + (\text{Area of } LTG/DZ \text{ complex peak})} \right] \times 100$$

Use of the Validated Method to Screen a Natural Sample for an Unknown "Hit" Compound A target of interest and a TBCL to the target are selected. As previously described, one determines the optimal incubation time and concentrations needed to mix the target and TBCL together to bind to the desired amount of available target (preferably, substantially all), and to produce a CE profile that observably differs from that of the target alone. Preferably, but not necessarily, the CE profile displays a decreased unbound target peak and may additionally display a prominent bound target/TBCL complex peak.

The target is mixed with a complex biological material sample to be screened, e.g., a natural extract or chemical mixture, for a time sufficient to allow binding of any hit compound present. A 5–60 minute incubation is usually adequate time to achieve such binding. A longer time is allowable.

A predetermined concentration of a TBCL that binds to the active site of the target is subsequently added to the target/sample mixture and incubated for the pre-determined optimal incubation time. The TBCL competes to bind all TBCL-binding sites of the target that are not bound by any unknown hit compound, and may bind TBCL-binding sites of the target from which the unknown hit compound momentarily dissociates, within the optimal incubation time allowed.

If no hit compound is present, substantially all of the target forms a stable complex with the TBCL. The target/TBCL complex is stable through the course of the subsequent CE run (at least until the detection point), which lasts less than the dissociation time of the target/TBCL complex. The resulting electropherogram pattern is no different from that of the control run without sample.

If a moderate-to-light-binding hit compound that binds to the TBCL binding site is present, less free target is available for binding to the TBCL. After the second incubation of the sample/target mixture with the TBCL, the resulting second mixture now contains two complexes: target/TBCL and target/MTBL along with any unbound target.

The mixture is then injected into an open-tube capillary system. Voltage is applied to begin the capillary electrophoresis.

In most cases, because moderate-to-tight binding hit compounds usually do not form complexes with the target that are stable for very long, the target/MTBL complex dissociates early in the CE run, which leaves only unbound target migrating in the capillary. The target/TBCL complex remains intact. Unbound target, target/TBCL complex and unbound TBCL are separated during CE due to differences in their electrophoretic mobilities. The migration pattern of the target is tracked, e.g., by monitoring UV or laser-induced fluorescence. Thus, in the presence of an MTBL, the unbound TG peak will be larger than in the control run without sample, and the target/TBCL complex peak will be smaller.

In a preferred embodiment, if a hit compound was not present in the screened sample, one observes preferably a single, target/TBCL complex peak showing that substantially all target is complexed (or if only unbound target can be seen during CE, one may observe a diminished unbound target peak).

If a detectable hit compound was present in the screened sample, one of several possibilities will be observed:

(a) If a moderate-to-tight-binding hit compound (MTBL) was present at a high concentration, there may be only one peak corresponding to unbound target. The target was unable to bind any TBCL during the second incubation step, because the hit compound was bound to all the target during the entire time that the target, sample, and TBCL were together. (FIGS. 4 and 5, discussed later, show this situation.) When the voltage was applied, the TBCL and any unbound target were quickly separated and unable to form a complex and the MTBL/target complex falls apart. Thus, the presence of a MTBL is inferred by a large unbound target peak.

(b) If a MTBL was present at a low concentration or if a more weakly binding hit compound was present in the sample, there may be two peaks representing unbound target peak (which is a larger peak than in the control run without sample present) and a bound target/TBCL complex peak, respectively. Some, but not all, of the target was available to bind the TBCL. Target availability occurred either because some of the target was never bound to the MTBL, or because some target dissociated from the hit compound and allowed the TBCL to bind during the optimal incubation time. (FIG. 6, discussed later, illustrates this situation).

One can demonstrate that the hit compound MTBL truly competes with the TBCL for binding to the TBCL-binding site of the target, by repeating the steps of the screening method but varying the incubation time of the sample TBCL mixture. In many cases, longer incubation times with the TBCL, prior to CE injection, result in the TBCL partially or completely replacing the hit compound if the hit compound binds more weakly than the TBCL. This results, in a preferred embodiment, in a decrease in any observed unbound target peak and a corresponding increase in any detectable target/TBCL complex peak over time. (FIGS. 6c and 7c show the different results occurring with differential incubation times of the target/screened sample mixture with the TBCL.) This result indicates a true competition between any unknown hit compound and the TBCL, which reduces the possibility, for example, that the sample has non-specifically destroyed the target, which made it unable to bind TBCL.

The method of the invention may also be used to estimate the relative binding affinity or concentration of any hit compound. This can be achieved by monitoring the rate at which the TBCL can displace the hit compound in the pre-capillary second incubation step. For example, starting with an amount of unknown hit that gives a 50% unbound target peak, one can incubate the sample for different times with the predetermined concentration of the TBCL prior to subjecting it to CE. For example, one can vary the incubation by increments of 10 minutes. If the unbound target peak is greatly reduced after a short incubation period with DZ, the unknown hit is probably not very strong or is strong but at a low concentration. However, if the unbound target peak is still relatively large after incubation with TBCL for a long period of time, this indicates that the unknown hit can "successfully" compete with the TBCL and that it is probably a strong binder (i.e., similar in binding strength to the TBCL) or a weaker binder present at a high concentration.

The screening method, particularly as exemplified, has good sensitivity in indirectly detecting the presence of MTBL and of weakly binding ligands in screened samples. Such ligands are "indirectly" detected in that although they dissociate from the target during CE, their presence is inferred by observed differences between the CE profiles of at least the unbound target peak in the sample/target/TBCL mixture and in a target/TBCL mixture. However, the method of the invention may also detect the presence of the following, additional types of hit compounds: (a) tight-binding hit compounds (e.q., complexes with a half-life greater than 1 minute) that bind to the TBCL-binding site of the target and have a different charge from that of the TBCL; (b) tight-binding, charged hit compounds that bind to sites other than the TBCL-binding site of the target; and (c) tight-binding, high MW compounds, charged or uncharged, that bind to any site on the target.

The present screening method may be used in conjunction with well-known techniques to assist in isolating any hit compound (s) in the screened sample. This can be accomplished by using the screening method to screen fractions generated through conventional isolation techniques (e.g., activity-guided fractionation). One of ordinary skill in the art will know how to employ standard purification, fractionation, separation, binding assay, and/or other techniques, along with additional screening assays of the invention, so as to identify and isolate the exact hit compound in the screened complex biological material that binds to the selected target.

The following examples are presented to illustrate the advantages of the present invention and to assist one of ordinary skill in the art in making and using the same. These examples are not intended in any way to limit the scope of the disclosure.

FIGS. 4–7 illustrate the results of different test runs of the screening assay of the invention using a known target, fluorescein-labeled human carbonic anhydrase II or HCA-II (hereinafter called "LTG," for labeled target); a TBCL to HCA-II, dorzolamide (DZ); and screened natural samples containing various test hit compound(s) or unknown ligand (s) that also bind to HCA-II, although at different affinities from DZ.

For all experiments depicted in FIGS. 4–7 as described below, the sample buffer was 100 mM of TES/Tris solution having a pH of 7.4 and containing 10 mg/ml of bovine serum albumin (BSA). The detectable target, LTG, was used at a concentration of 5 nM in all samples, as described below. The capillary electrophoresis (CE) apparatus used was a Beckman P/ACE Model fitted with an argon laser capable of 488 nm excitation and a fluorescence detector. The running or background buffer used in the CE apparatus was 50 mM of CAPSO/Tris solution buffered to a pH of 9.2. In each CE run, an aliquot of the material to be CE-fractionated was pressure injected for 10 seconds into a polyvinylalcohol-coated capillary having a 50-$\mu$ inner diameter and a 27-cm length. The detector was placed at 20 cm along the capillary length. A voltage of 25 kV was applied, and the detector was set to detect fluorescence at 520 nm.

EXAMPLE I

Figure 4A:
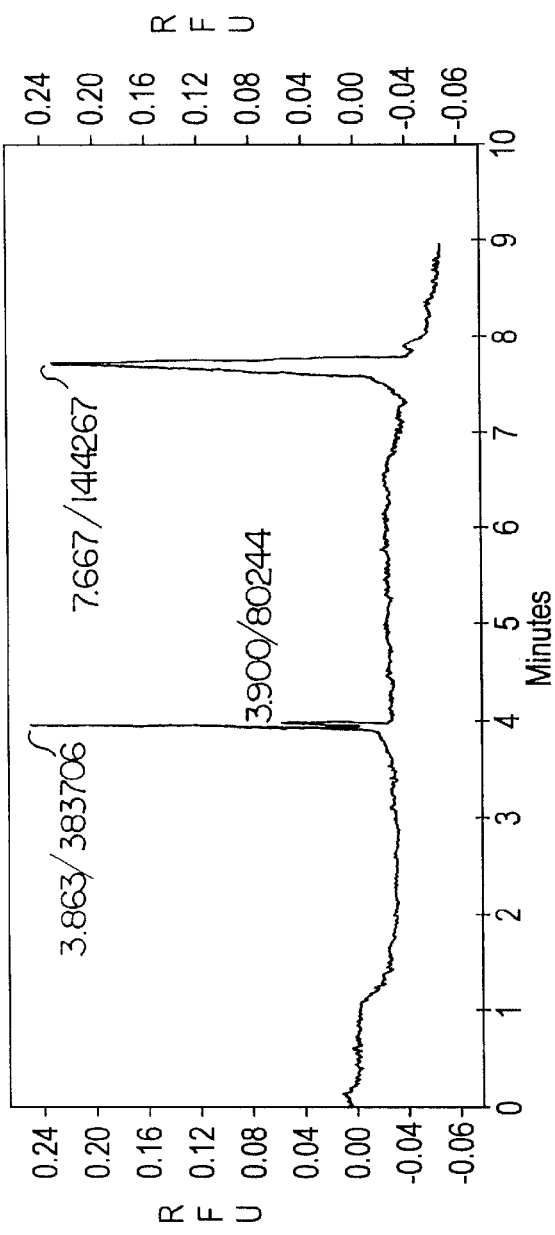
FIG. 4, panel [A] depicts the CE profile of a fluorescently labeled target alone, 5 nM of fluorescein-labeled human carbonic anhydrase II or HCA-II (hereinafter called "LTG"); panel [B] shows the CE profile of the LTG substantially completely bound to a TBCL, 2 nM dorzolamide (DZ), after a 1-minute incubation; panel [C] shows the CE profile of a combination of the LTG after incubation with, first, a sample of complex, biological material (natural sample) lacking a natural hit but spiked with a test hit compound, 100 nM ethoxyzolamide (EZ), and subsequently, mixed and incubated with the TBCL, 2 nM DZ (incubation occurring prior to CE)
Figure 4B:
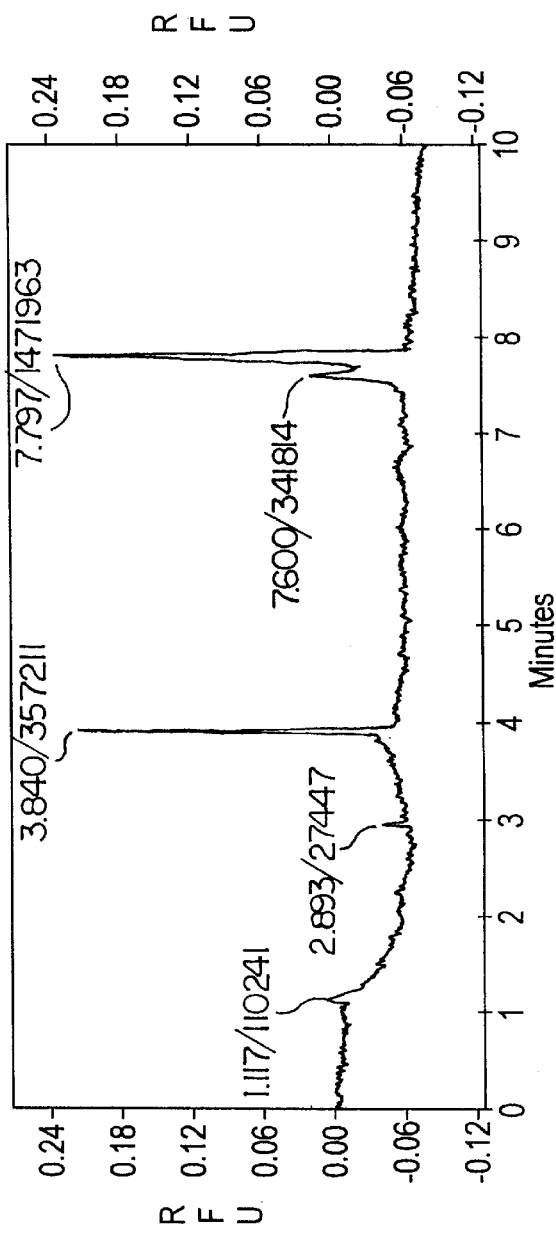
Figure 4C:
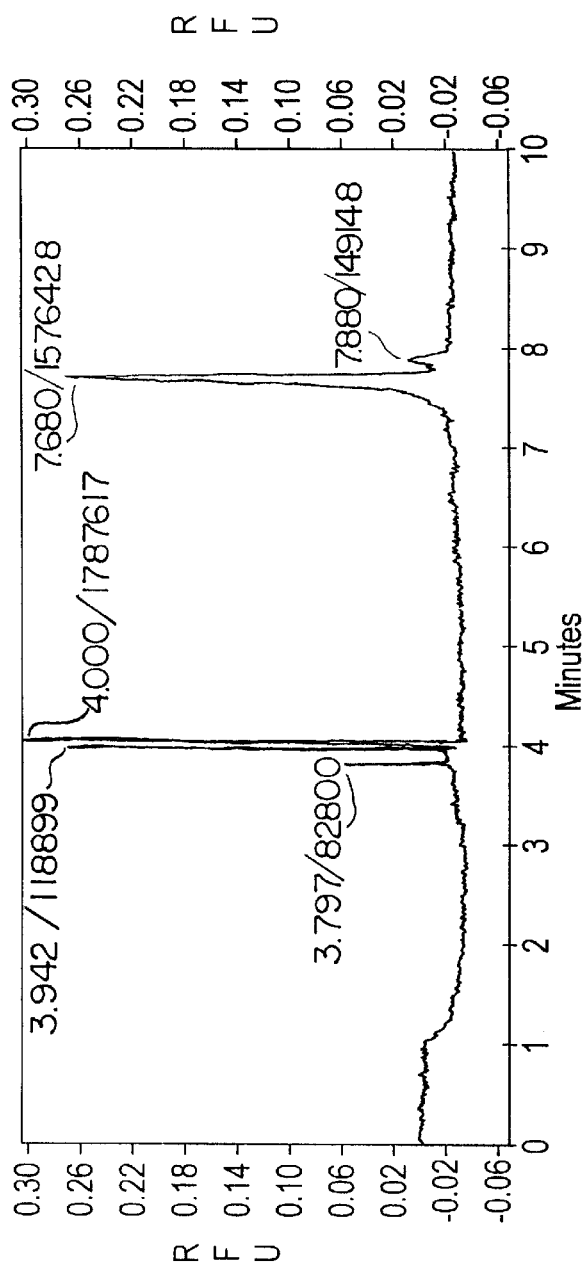

The screening assay runs in FIG. 4 used 5 nM of HCA-II (LTG); 2 nM of its TBCL, dorzolamide (DZ); and a screening sample containing an inert natural extract, at 10% volume by volume (v/v) spiked with a test hit compound, ethoxyzolamide (EZ) that binds to HCA-II. Ethoxyzolamide (EZ) has a moderate binding affinity for HCA-II (EZ is an MTBL), in contrast to DZ's tight-binding affinity.

Panel [A] of FIG. 4 depicts the CE profile of a sample of 5 nM LTG, alone. A major peak representing unbound HCA-II (LTG) occurs at 7.667 minutes during the CE run. The early sharp peak at 3.663 minutes is an artifact peak.

For panel [B] of FIG. 4, a 5 nM sample of the LTG was incubated for 1 minute with 2 nM DZ, the TBCL. An aliquot of that sample was then subjected to CE. Panel [B] of FIG. 4 shows a major peak at 7.797 minutes, representing the complex of DZ bound to LTG. A minor peak corresponding to a small amount of unbound LTG is observed at 7.600 minutes.

For panel [C] of FIG. 4, a 5 nM LTG sample was first incubated for at least 5 minutes with the test sample screened—a sample containing 10% v/v of inert natural extract spiked with a test hit compound, 100 nM ethoxyzolamide (EZ)—and subsequently, with 2 nM of DZ for 1 minute (the optimal incubation time). Panel [C] shows the CE profile of a mixture of LTG, the test sample, and DZ. Incubation of the fluorescently LTG target with EZ first, allowed EZ to bind to the LTG and to prevent the LTG from binding to the TBCL, DZ in the second incubation step containing all three compounds. However, the target/hit compound complex formed by the target LTG and the moderately binding ligand or test hit compound, EZ, was not stable and dissociated once injected into the CE apparatus. As a result, in panel [C] of FIG. 4, the LTG that was bound to EZ before CE injection, appears as unbound LTG during CE. Therefore, the CE profile shows the substantial reduction of the LTG/DZ complex peak at 7.880 minutes and the appearance of a much higher, unbound LTG peak at 7.680 minutes (in contrast to panel [B] of FIG. 4). This panel [C] example served as a positive control showing the effectiveness of the present method in detecting moderate-binding ligands.

EXAMPLE II

Figure 5A:
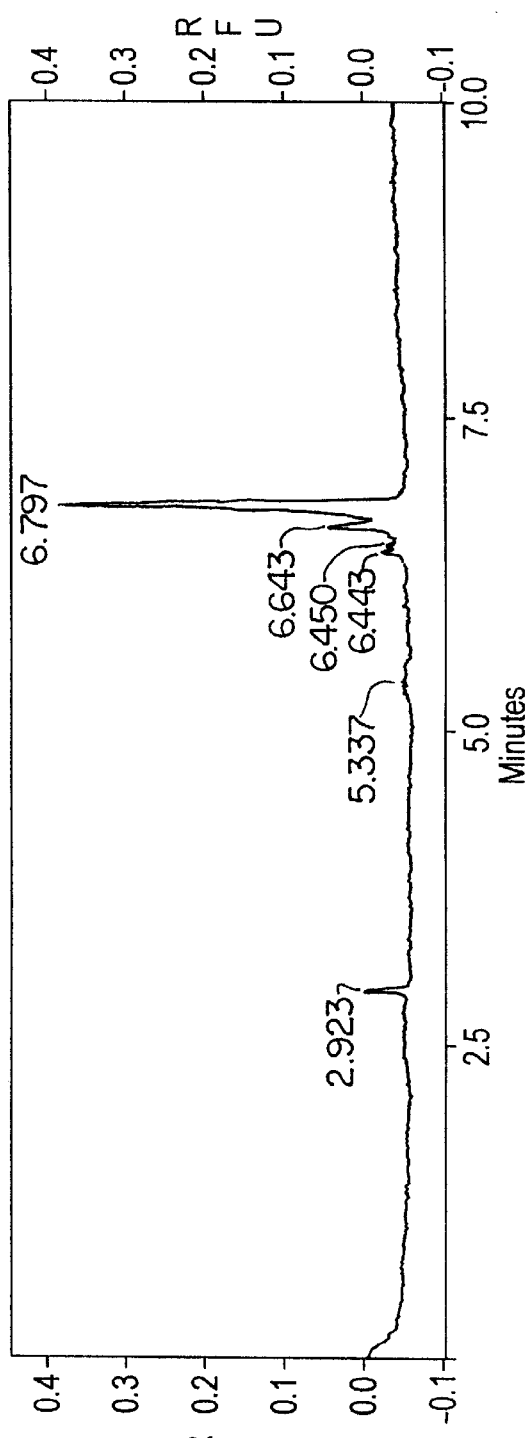
FIG. 5, panel [A] depicts the CE profile of the LTG bound to the TBCL, DZ; panel [B] shows the CE profile of a mixture of 5 nM LTG incubated first with 10% v/v natural sample that contains an unknown natural hit compound and, subsequently, with 2 nM DZ for one minute (incubation occurring prior to CE)
Figure 5B:
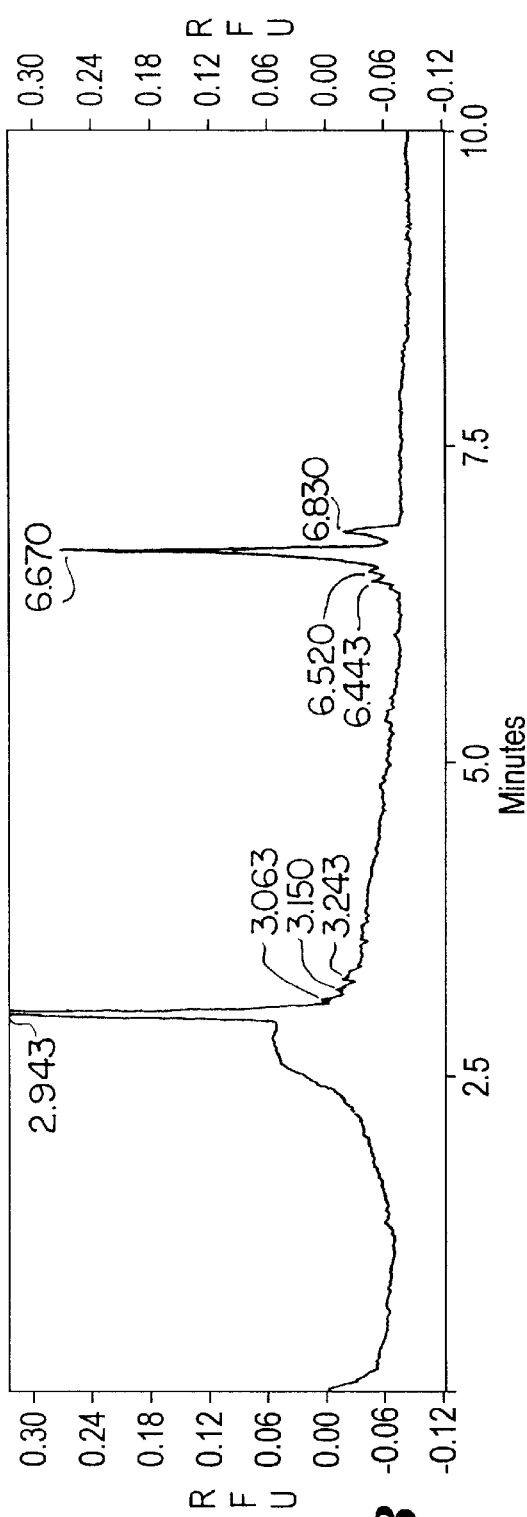

FIG. 5 depicts the results of another run of the screening assay according to the present invention. The conditions were the same as for the experiments in FIG. 4, except that the screened sample was a 10% v/v natural extract sample that was not spiked with ethoxyzolamide. Instead, the natural sample here was found to contain an unknown hit compound that competed with the known ligand, DZ, in binding to the LTG.

Panel [A] of FIG. 5, the negative control for this run, depicts the same conditions as in panel [B] of FIG. 4, with 5 nM of labeled LTG incubated with 2 nM of DZ, prior to CE. A major peak corresponding to the bound target/TBCL (LTG/DZ) complex was seen at 6.797 minutes. A minor peak corresponding to a small amount of unbound LTG was detected at 6.643 minutes.

Panel [B] of FIG. 5 shows the CE results after incubation of 5 nM LTG with the 10% v/v natural extract sample for 10 minutes and, subsequently, with 2 nM DZ for one minute prior to CE. Aside from the absence of any EZ, the conditions for this experiment were the same as for panel [C] of FIG. 4. The bound target/TBCL (LTG/DZ) complex peak at 6.830 minutes was observed to be greatly reduced because less LTG was available for binding to DZ, due to the presence of a hit compound bound to LTG prior to the addition of DZ. Thus, a large unbound LTG peak appeared at 6.670 minutes, which was much larger than the reduced LTG/DZ peak. The unbound LTG peak indicated the presence of an unknown hit compound in the screened natural extract sample that could bind to LTG. Also observed was a series of peaks spread broadly over the region of 2.5–3.5 minutes, representing unknown fluorescent peaks in the natural extract. This result points out the sensitivity and power of the present method. If this screen had not been a CE separation technique and had been done in a microtiter well, the fluorescent background peaks would have been undistinguishable from a target peak and would have given a false positive (or negative) result in a fluorescence-based binding assay.

EXAMPLE III

Figure 6A:
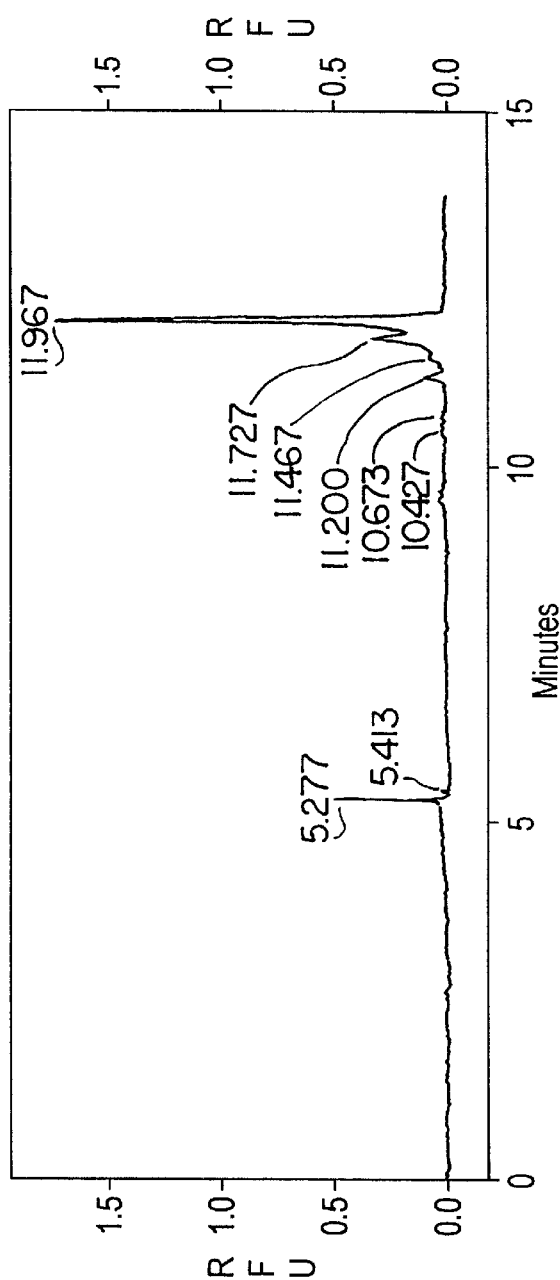
FIG. 6, panel [A] depicts the CE profile of 5 nM LTG after a 1-minute incubation with 2 nM DZ; panel [B] shows the CE profile of 5 nM of LTG incubated first with a natural sample containing 10 nM of ethoxyzolamide (EZ) and then for 1 minute with 2 nM dorzolamide (DZ); panel [C] shows the CE profile of an aliquot of the same mixture as in panel [B], after being subjected to an additional 20 minutes of incubation time with DZ, prior to CE.
Figure 6B:
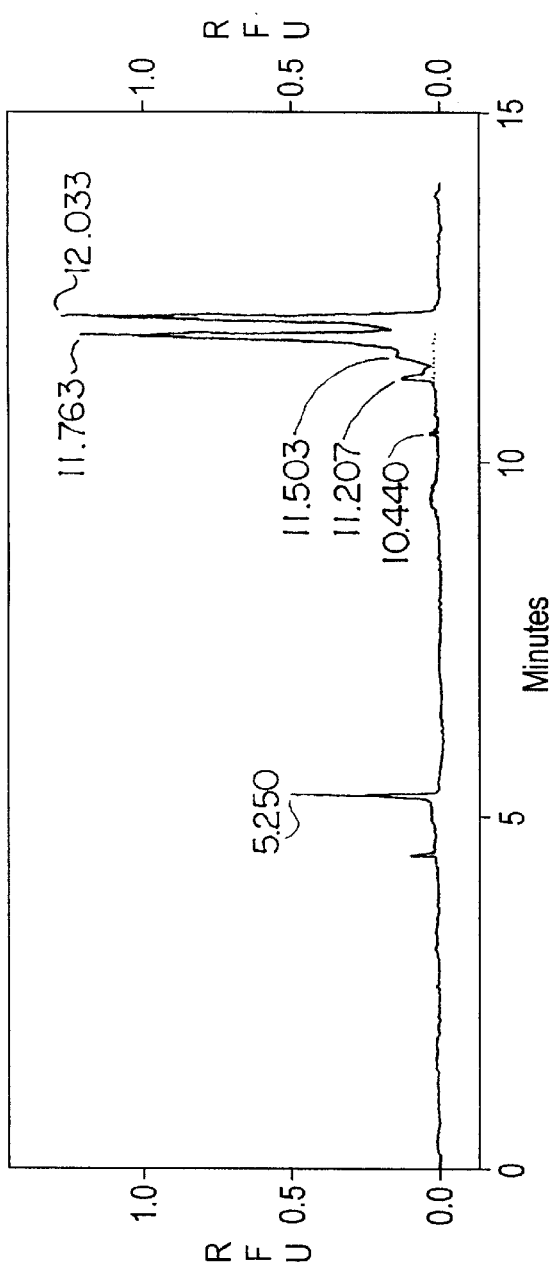
Figure 6C:
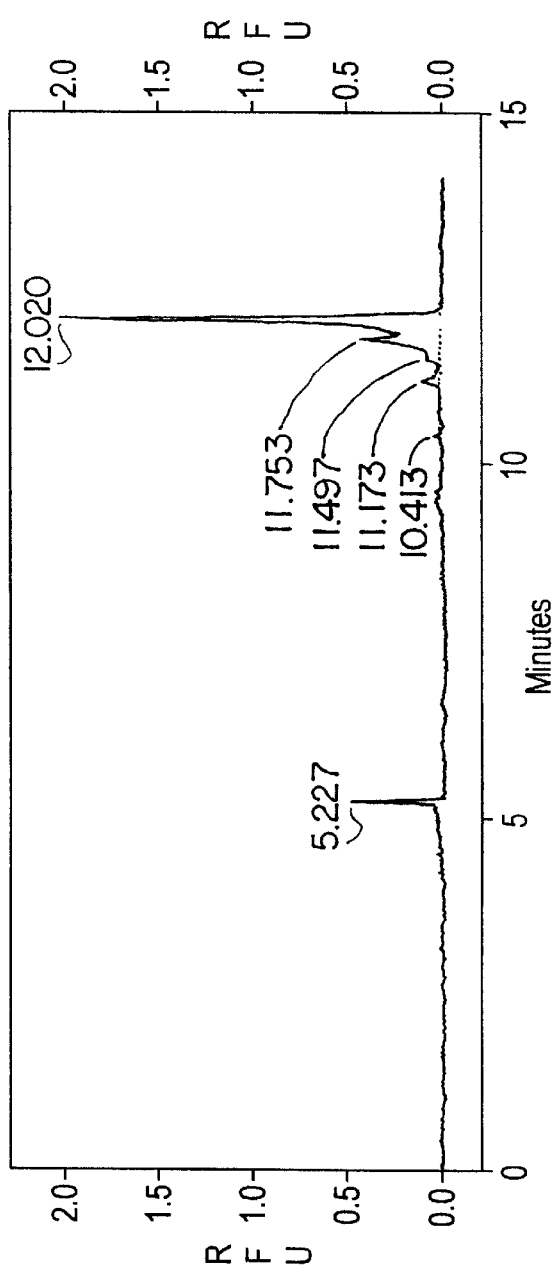

FIG. 6 depicts the CE results of another test run of the present screening assay, under similar conditions as in Example I, except that the screened inert sample contained 10 nM (instead of 100 nM) of the test hit compound EZ. As well, two different pre-CE incubation times with the TBCL were tested.

Panel [A] of FIG. 6 depicts the CE profile of 5 nM LTG after a 1-minute incubation with 2 nM DZ. As before, a major peak corresponding to the TBCL/DZ complex is seen at 11.987 minutes. A minor peak corresponding to unbound, LTG is seen at 11.727 minutes.

In panel [B] of FIG. 6, 5 nM of LTG was incubated first with an inert natural sample spiked with 10 nM of ethoxyzolamide (EZ) for 10 minutes, and then with 2 nM dorzolamide (DZ) for 1 minute. Due to competitive binding of the target by the test hit compound, EZ, the LTG/DZ complex peak at 12.033 minutes was reduced, while the unbound target peak at 11.763 minutes was higher. Therefore, prior binding of the EZ to the LTG prevented some, but not all, LTG from binding to the DZ during the later, 1-minute incubation with DZ.

Panel [C] of FIG. 6 shows the capillary electrophoresis profile of a sample of the same mixture as in Panel [B] of FIG. 6, (5 nM LTG with 10 nM EZ-containing natural sample, and then with TBCL, 2 nM DZ). However, the mixture is subjected to an additional 20 minutes of incubation time with DZ, prior to CE. That extra incubation time allowed the tight-binding DZ ligand to almost completely displace bound EZ from the LTG prior to injection into the CE apparatus. Therefore, the resulting. CE profile showed a higher target/LTG/DZ complex peak at 12.020 minutes and a greatly reduced peak of unbound LTG at 11.753 minutes (in comparison to panel [B] of FIG. 6). Thus, as demonstrated, this method can be used to show that a detectable unknown hit compound specifically competes with the TBCL. For example, one could claim that a screened natural sample displaying a "hit"—e.g., a sample that alters target mobility by producing a difference in peak area, location, or shape—is simply destroying the activity of some of the target (LTG), which thus can no longer bind the TBCL (DZ). Panel [C] of FIG. 6 proves that the LTG remains functionally active during the screening method, because given enough incubation time (of the sample/LTG/DZ mixture), DZ replaces the test hit compound EZ in binding to LTG.

EXAMPLE IV

Figure 7A:
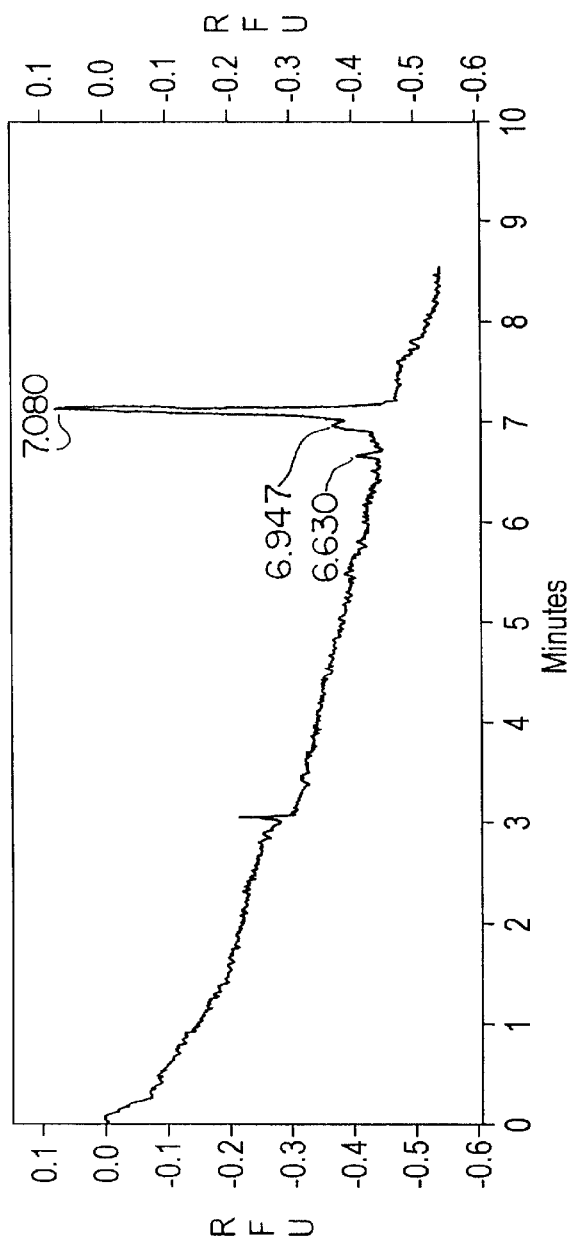
FIG. 7, panel [A] depicts the CE profile of 5 nM LTG incubated with 2 nM DZ; panel [B] shows the CE profile of 5 nM LTG after incubation with a natural sample that contains an unknown hit compound and then for 1 minute with 2 nM DZ; panel [C] shows the CE profile of the same sample as in [B] after an additional 20 minutes of incubation time with DZ prior to CE.
Figure 7B:
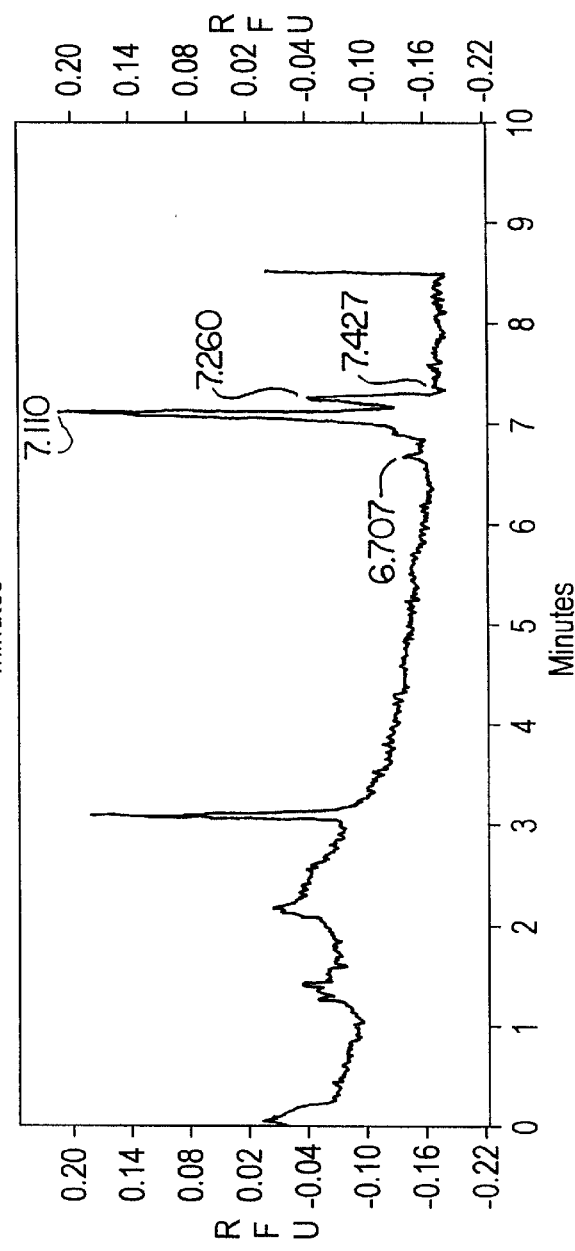
Figure 7C:
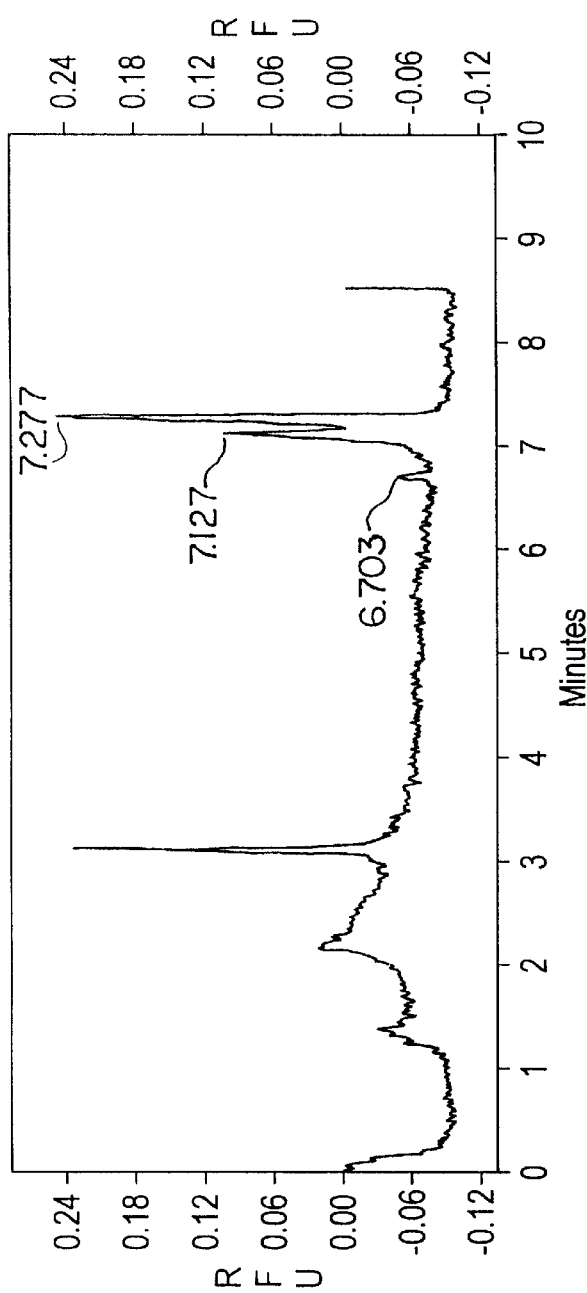

FIG. 7, panel [A] depicts the CE profile of 5 nM LTG incubated with 2 nM DZ, under the same conditions as for FIG. 4, panel [B]. A major peak corresponding to the LTG/DZ complex was seen at 7.080 minutes. A minor peak corresponding to unbound LTG was seen at 6.947 minutes.

Panel [B] of FIG. 7 shows the CE profile of 5 nM LTG after incubation with a natural sample that contains an unknown hit compound and then with the TBCL, DZ, under the same conditions as above. The LTG/DZ complex peak at 7.260 minutes was reduced, while the unbound LTG peak at 7.110 minutes was higher.

Panel [C] of FIG. 7 shows the CE profile of an aliquot of the same mixture as for FIG. 7, panel [B], after an additional 40 minutes of incubation with DZ prior to injection into the CE apparatus. DZ has displaced some but not all of the hit compound from being bound to LTG, and a higher LTG/DZ complex peak is seen at 7.277 minutes and a reduced unbound LTG peak is seen at 7.127 minutes. These results show that the screening assay has detected a tight-binding hit, or a moderate-to-weak binding hit at a high concentration, since DZ was unable to completely replace the hit compound even after another 40 minutes of incubation (as opposed to FIG. 7, panel [A]'s 1-minute incubation).

EXAMPLE V

This example illustrates the case where a tight-binding hit compound that has a different charge from, or a higher MW than, the TBCL, is present in the natural sample.

Figure 8A:
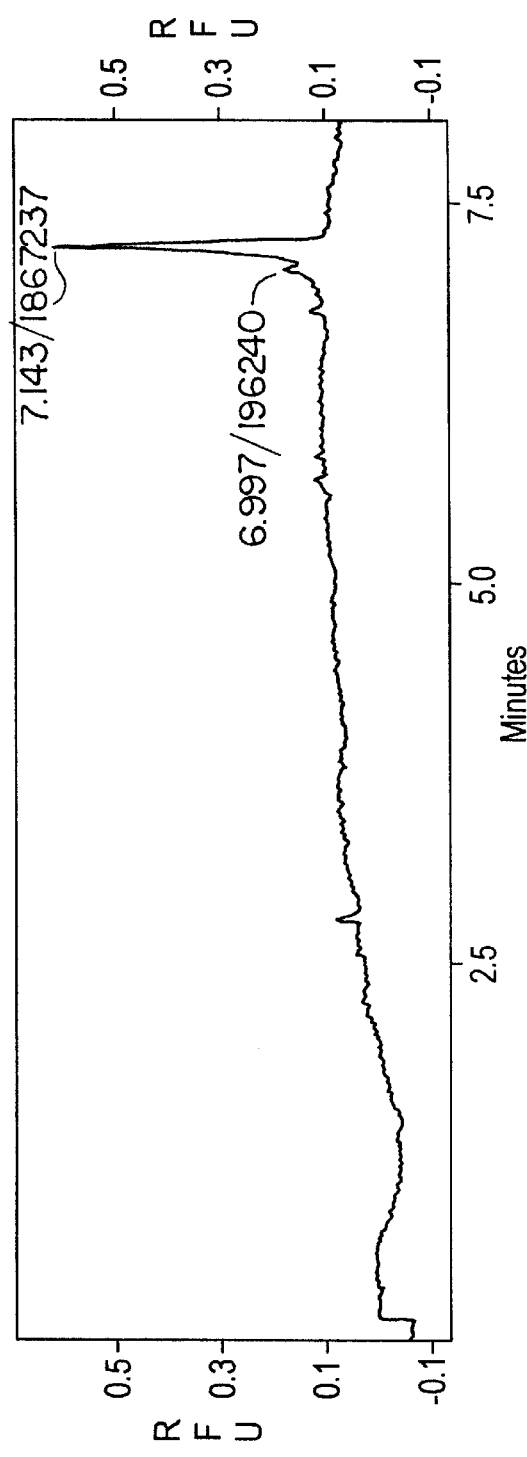
FIG. 8, panel [A] depicts the CE profile of 5 nM LTG after 1 minute incubation with 2 nM DZ as the TBCL; panel [B] shows the CE profile of 5 nM LTG incubated with, first, a natural sample containing an unknown, tight-binding hit compound with a different charge than DZ, and then for 1 minute with 2 nM DZ.
Figure 8B:
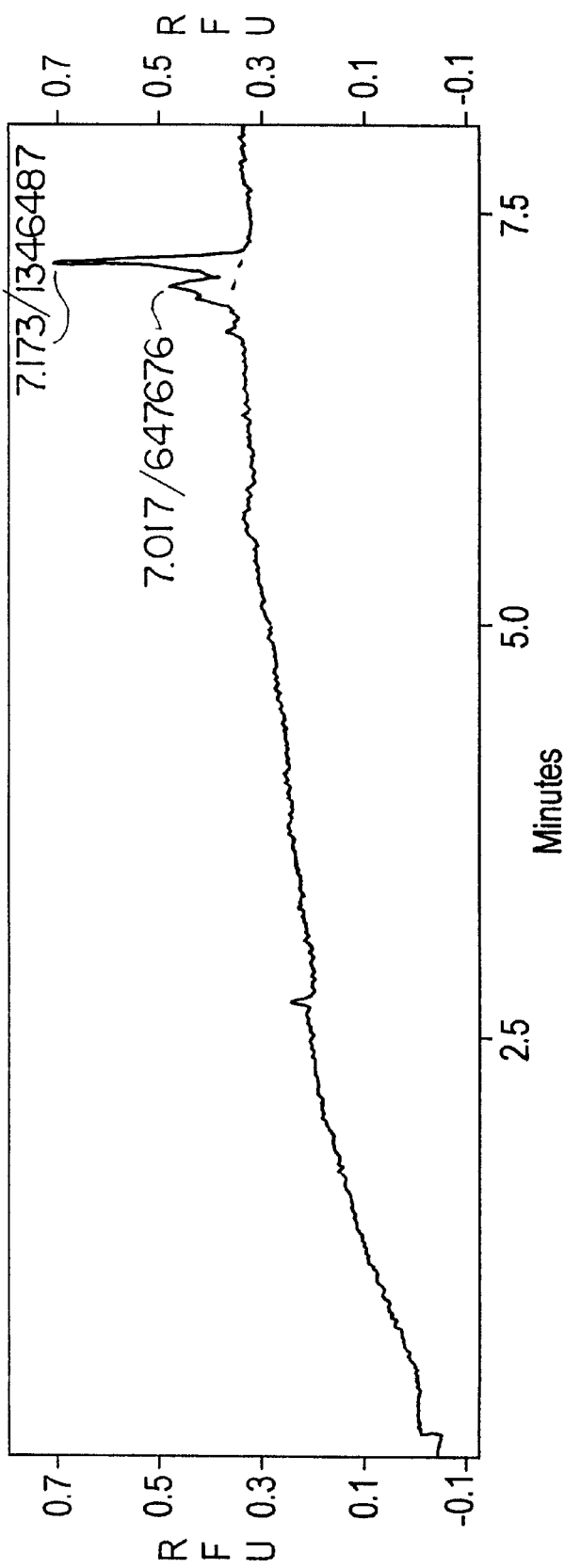

Panel [A] of FIG. 8 depicts the CE profile of 5 nM LTG incubated with 2 nM DZ. A major peak corresponding to the LTG/DZ complex is seen at 7.143 minutes. A minor peak corresponding to the unbound LTG is seen at 6.997 minutes.

Panel [B] of FIG. 8 shows 5 nM LTG incubated with a natural sample that contains an unknown, tight-binding hit compound, and then incubated with 2 nM DZ for the optimal incubation time. As seen in the figure, most of the LTG was complexed to DZ because the LTG/DZ peak at 7.173 minutes is still large. The minor unbound LTG peak at 7.017 minutes is still present. However, a new peak is now visible on the left-hand shoulder of the unbound LTG peak. This shoulder peak is a stable complex of LTG with an unknown hit compound in the natural sample that has a different (opposite) charge from that of the TBCL (DZ). The opposite charge on the unknown hit makes the complex appear at an earlier time than the unbound LTG, rather than at a later time like the LTG/DZ complex.

This screening method has successfully detected a wide variety of hit compounds having different charges (negative, neutral, or positive) and different binding affinities to the target molecule, human carbonic anhydrase II (HCA-II). For instance, it has detected moderately binding hit compounds such as 0.5 nM of ethoxyzolamide and 2.0 nM of dichlorphenamide. Weak-binding hit compounds detected include 80 nM of acetazolamide and 150 nM of methazolamide. The method has also detected a very weak-binding hit compound, carzenide (PCBS) at a 30,000 nM concentration. See, e.g., FIG. 9 for calibration curves of different concentrations of different hit compounds binding to the HCA-II target.

While the present invention has been described in conjunction with preferred embodiments, one of ordinary skill in the art, after reading the foregoing specification, will be able to effect various changes, substitutions of equivalents, and other alterations to the compositions and methods set forth herein.

What is claimed is:

1. A method of screening complex biological material for previously unidentified, weak-to-tight-binding hit compounds that bind to a pre-selected, detectable target, comprising, in the order given, the steps of:

(1) providing a sample of complex biological material;

(2) mixing said sample of complex biological material with a predetermined concentration of said target to form a first, sample/target mixture;

(3) mixing said first mixture with a predetermined concentration of a known, tight-binding, competitive ligand that binds to said target, to form a second, sample/target/known ligand mixture, and incubating said second mixture for a predetermined optimal incubation time;

(4) injecting an aliquot of said second mixture into a capillary electrophoretic apparatus;

(5) subjecting said aliquot to capillary electrophoresis;

(6) tracking the capillary electrophoreric migration of the target in said aliquot, by detecting target, whether bound or unbound, upon capillary electrophoresis, to generate a capillary electrophoretic migration pattern of the target in the aliquot;

(7) determining whether the migration pattern of the target in said aliquot differs from a reference standard, thereby indicating the presence of a hit compound that binds to said target, wherein said predetermined target concentration, said predetermined known ligand concentration, and said predetermined optimal incubation time have been predetermined in a separate optimization process, wherein the reference standard comprises a capillary electrophoretic migration pattern of the target obtained by detecting target, whether bound or unbound, during capillary electrophoresis of an aliquot of a mixture of the predetermined concentration of the target and the predetermined concentration of the known, tight-binding competitive ligand, in an absence of any other target-binding ligand, wherein said predetermined known ligand concentration suffices to bind enough of said predetermined target concentration so that the reference standard detectably differs from a capillary electrophoretic migration pattern of unbound target alone, and wherein said predetermined optimal incubation time is a shortest amount of time needed to incubate the predetermined concentrations of target and known, tight-binding ligand together to produce the desired reference standard, said optimal incubation time being less than an incubation time needed to allow equilibrium binding between the predetermined target concentration and predetermined known ligand concentration.

2. The method of claim 1, wherein said predetermined target concentration was determined, during the optimization process, by:

either performing capillary electrophoresis of different concentrations of said target in an absence of any target-binding ligand and selecting the target concentration that produces a detectable capillary electrophoretic peak representing unbound target; or performing capillary electrophoresis of the target with the known ligand and selecting the target concentration that produces a detectable capillary electrophoretic peak representing bound target/known ligand complex.

3. The method of claim 2, wherein said predetermined target concentration, upon capillary electrophoresis in the absence of any target-binding ligand, produced a capillary electrophoretic peak representing unbound target and having an amplitude at least three times above a baseline representing background noise.

4. The method of claim 1, wherein said predetermined known ligand concentration was determined, during said optimization process, by mixing said predetermined target concentration with different concentrations of said known ligand, subjecting an aliquot of each resulting target/known ligand mixture to capillary electrophoresis, and selecting a concentration that is twice the smallest concentration of said known ligand that binds enough of said target in said predetermined concentration to produce a detectable difference in said target's capillary electrophoretic migration pattern, as compared to the migration pattern of unbound target alone.

5. The method of claim 4, wherein said predetermined known ligand concentration produced at least a 10% difference in peak area between a peak in said target's capillary electrophoretic migration pattern and a corresponding peak in the migration pattern of unbound target alone.

6. The method of claim 4, wherein said predetermined known ligand concentration produced at least a 50% difference in peak area between a peak in said target's capillary electrophoretic migration pattern and a corresponding peak in the migration pattern of unbound target alone.

7. The method of claim 4, wherein said predetermined known ligand concentration produced at least a difference in peak area of about 90–99% between a peak in said target's capillary electrophoretic migration pattern and a corresponding peak in the migration pattern of unbound target alone.

8. The method of claim 1, wherein said optimal incubation time is within a range of about 0.5–5.0 minutes.

9. The method of claim 1, wherein said optimal incubation time is within a range of about 0.75–1.0 minute.

10. The method claim 1, wherein said detectable target is a member selected from the group consisting of enzymes, proteins, polypeptides, nucleic acids, polynucleotides, carbohydrates, and chemically, enzymatically, or recombinantly modified forms thereof, wherein said modified forms have been modified for improved electrophoretic properties.

11. The method of claim 1, wherein said known, tight-binding competitive ligand is a member selected from the group consisting of natural compounds, synthetic compounds, antibodies, and drugs known to bind to the target of interest.

12. The method of claim 1, wherein said complex biological material comprises at least one member selected from the group consisting of combinatorial chemical library, extracts of terrestrial plants, extracts of marine plants, cells from higher animals including humans, eubacteria, actinomycetes, bacteria, extracts from non-recombinant or recombinant microorganisms, microbial fermentation broths, fungi, protozoa, algae, archaebacteria, worms, insects, marine organisms, sponges, corals, crustaceans, viruses, phages, tissues, organs, blood, soil, sea water, water from a fresh-water body, humus, detritus, manure, mud, and sewage or partially purified fractions thereof.

13. The method of claim 1, further comprising, prior to step (1), subjecting said sample of complex biological material to at least one pretreatment step, said pretreatment being freeze-thawing, homogenization, sonication, microwave extraction, heating, solvent extraction, filtration, fractionation, or dilution.

14. The method of claim 1, wherein the migration of said target, whether bound or unbound, is tracked during capillary electrophoresis by detection of UV- or laser-induced fluorescence, UV absorption, or visible light absorption.

15. The method of claim 1, wherein said capillary electrophoretic apparatus is a microfabricated device.

16. The method of claim 1, wherein said capillary electrophoretic apparatus is coupled to an on-line detection instrument.

17. The method of claim 1, wherein said known ligand forms a stable complex with said target that does not dissociate during the capillary electrophretic run of step (5).

18. The method of claim 17, wherein said capillary electrophoretic run has a duration of two hours or less.

19. The method of claim 17, wherein said capillary electrophoretic run has a duration of about 0.5–10 minutes.

20. The method of claim 1, wherein said known ligand is charged, has a significantly higher molecular weight than the target, or both, such that the bound target/known ligand complex has a different charge-to-mass ratio from that of the unbound target.

21. The method of claim 1, wherein a capillary of said capillary electrophoretic apparatus has a diameter within a range of about 10 to 500 microns and a length within a range of about 0.5 cm to 1.0 m.

22. The method of claim 1, wherein a capillary of said capillary electrophoretic apparatus has an inside wall coating that minimizes adsorption of said target, said known ligand, or a complex of said target and said known ligand to said capillary.

23. The method of claim 1, wherein said first sample/target mixture is incubated for about 5–10 minutes.

24. The method of claim 1, wherein a difference in the migration pattern comprises at least one member selected from the group consisting of: a difference in an area of a selected capillary electrophoretic peak; an absence in the migration pattern of a capillary electrophoretic peak that is present in the reference standard; and an appearance of a capillary electrophoretic peak not present in the reference standard.

25. The method of claim 24, wherein the difference in migration pattern comprises a difference in the area of a selected capillary electrophoretic peak, said difference in area comprising a member selected from the group consisting of: an increased area in a peak representing unbound target; and a decreased area in a peak representing bound target/known ligand complex.

26. The method of claim 24, wherein the difference in the migration pattern comprises the appearance of a new peak representing a target/hit compound complex.

27. The method of claim 1, wherein the difference in the migration pattern comprises the difference in migration time of detected target, whether bound or unbound, between the reference standard and the migration pattern obtained in step (6).

28. The method of claim 1, wherein the reference standard further comprises capillary electrophoretic peaks representing independent markers whose migration times are known to flank that of the target.

29. A method of screening complex biological material for previously unidentified, weak-to-tight-binding hit compounds that bind to a pre-selected, detectable target, comprising, in the order given, the steps of:
(1) providing a sample of complex biological material;
(2) fractionating said sample into multiple fractions;
(3) mixing one of said multiple fractions with a predetermined concentration of said target to form a first, sample fraction/target mixture;
(4) mixing said first mixture with a predetermined concentration of a known, tight-binding, competitive ligand that binds to said target, to form a second, sample fraction/target/known ligand mixture, and incubating said second mixture for a predetermined optimal incubation time;
(5) injecting an aliquot of said second mixture into a capillary electrophoretic apparatus;
(6) subjecting said aliquot to capillary electrophoresis;
(7) tracking the capillary electrophoretic migration of the target in said aliquot, by detecting the target, whether bound or unbound, upon capillary electrophoresis, to generate a capillary electrophoretic migration pattern of the target in said aliquot;
(8) determining whether the migration pattern of the target in said aliquot differs from a reference standard, thereby indicating the presence of a hit compound that binds to said target; and
(9) repeating steps (3)–(8) with each of the fractions generated in step (2);
wherein said predetermined target concentration, said predetermined known ligand concentration, and said predetermined optimal incubation time have been predetermined in a separate optimization process,
wherein the reference standard comprises a capillary electrophoretic migration pattern of the target obtained by detecting target, whether bound or unbound, during capillary electrophoresis of an aliquot of a mixture of the predetermined concentration of the target and the predetermined concentration of the known, tight-binding competitive ligand, in an absence of any other target-binding ligand,
wherein said predetermined known ligand concentration suffices to bind enough of said predetermined target concentration so that the reference standard detectably differs from a capillary electrophoretic migration pattern of unbound target alone, and
wherein said predetermined optimal incubation time is a shortest amount of time needed to incubate the predetermined concentrations of target and known, tight-binding ligand together to produce the desired reference standard, said optimal incubation time being less than an incubation time needed to allow equilibrium binding between the predetermined target concentration and predetermined known ligand concentration.

30. The method of claim 1 or 29, further comprising, subsequent to a last recited step, further fractionating a sample or sample fractions demonstrating the presence of a hit compound that binds to said target.

31. The method of claim 30, further comprising, subsequent to said fractionation step of claim 29, isolating said hit compound from said complex biological material.

32. A method of determining a relative binding strength or concentration of a hit compound that hinds to a pre-selected, detectable target, comprising:
(1) providing a sample comprising a hit compound;
(2) mixing said sample with a predetermined concentration of said target to form a first, sample/target mixture;
(3) mixing said first mixture with a predetermined concentration of a known, tight-binding, competitive ligand that binds to said target, to form a second, sample/target/known ligand mixture, and incubating said second mixture for a predetermined incubation time;
(4) injecting an aliquot of said second mixture into a capillary electrophoretic apparatus;
(5) subjecting said aliquot to capillary electrophoresis;
(6) tracking the capillary electrophoretic migration of the target in said aliquot, by detecting the target, whether bound or unbound, upon capillary electrophoresis, to generate a migration pattern of the target in said aliquot;
(7) determining whether the migration pattern of the target in said aliquot differs from a reference standard, thereby indicating the presence of a hit compound that binds to said target;

(8) repeating, at least once, steps (3)–(7), using a different pre-determined incubation time in each repeat of step (3); and (9) comparing the migration patterns generated by the repeats of steps (3)–(7), to monitor the rate at which said known, tight-binding, competitive ligand displaces said hit compound from binding to said target, upon longer incubation of the second mixture;

wherein said predetermined target concentration, said predetermined known ligand concentration, and said predetermined optimal incubation time have been predetermined in a separate optimization process, wherein the reference standard comprises a capillary electrophoretic migration pattern of the target obtained by detecting target, whether bound or unbound, during capillary electrophoresis of an aliquot of a mixture of the predetermined concentration of the target and the predetermined concentration of the known, tight-binding competitive ligand in an absence of any other target-binding ligand, wherein said predetermined known ligand concentration suffices to bind enough of said predetermined target concentration so that the reference standard detectably differs from a capillary electrophoretic migration pattern of unbound target alone, wherein said predetermined incubation time in a first performance of step (3) is a shortest amount of time needed to incubate the predetermined concentrations of target and known, tight-binding ligand together to produce the desired reference standard, said predetermined incubation time in the first performance of step (3) being less than an incubation time needed to allow equilibrium binding between the predetermined target concentration and predetermined known ligand concentration.

* * * * *

UNITED STATES PATENT AND TRADEMARK OFFICE
CERTIFICATE OF CORRECTION

PATENT NO.    : 6,299,747 B1
DATED         : October 9, 2001
INVENTOR(S)   : Yuriy M. Dunayevskiy et al.

It is certified that error appears in the above-identified patent and that said Letters Patent is hereby corrected as shown below:

Column 4,
Line 31, "a pattern;" should read -- pattern; --;

Column 12,
Line 58, "Electrothoresis" should read -- Electrophoresis --;

Column 18,
Line 25, " "Hit Compounds") " should read -- "Hit Compound") --;

Column 21,
Line 16, "e.q.," should read -- e.g., --;

Column 23,
Line 45, "resulting." should read -- resulting --;

Column 24,
Line 52, "(PCBS)" should read -- (pCBS) --;

Column 28,
Line 44, "claim 29" should read -- claim 30 --; and
Line 47, "hinds" should read -- binds --.

Signed and Sealed this

Twenty-ninth Day of April, 2003

JAMES E. ROGAN
*Director of the United States Patent and Trademark Office*